US012698524B2

(12) United States Patent
Nagano et al.

(10) Patent No.: US 12,698,524 B2
(45) Date of Patent: Aug. 4, 2026

(54) KIT FOR TOGETHER DETECTING MULTIPLE TARGET NUCLEIC ACIDS DIFFERING FROM EACH OTHER AND DETECTION METHOD USING THE SAME

(71) Applicant: MIZUHO MEDY CO., LTD., Saga (JP)

(72) Inventors: Takashi Nagano, Saga (JP); Kensuke Miyajima, Saga (JP); Kenji Narahara, Saga (JP)

(73) Assignee: MIZUHO MEDY CO., LTD., Saga (JP)

( * ) Notice: Subject to any disclaimer, the term of this patent is extended or adjusted under 35 U.S.C. 154(b) by 677 days.

(21) Appl. No.: 17/205,364

(22) Filed: Mar. 18, 2021

(65) Prior Publication Data

US 2021/0238653 A1    Aug. 5, 2021

Related U.S. Application Data

(62) Division of application No. 15/576,923, filed as application No. PCT/JP2016/063831 on May 10, 2016, now abandoned.

(30) Foreign Application Priority Data

Jun. 4, 2015    (JP) ................................. 2015-113979

(51) Int. Cl.
| | |
|---|---|
| *C12Q 1/68* | (2018.01) |
| *C12Q 1/6816* | (2018.01) |
| *C12Q 1/686* | (2018.01) |
| *C12Q 1/689* | (2018.01) |

(52) U.S. Cl.
CPC .............. *C12Q 1/686* (2013.01); *C12Q 1/68* (2013.01); *C12Q 1/6816* (2013.01); *C12Q 1/689* (2013.01)

(58) Field of Classification Search
CPC ....................................................... C12Q 1/68
See application file for complete search history.

(56) References Cited

U.S. PATENT DOCUMENTS

| | | | | |
|---|---|---|---|---|
| 2002/0106653 A1* | 8/2002 | Kurane | ................ | C12Q 1/6851 534/727 |
| 2004/0023207 A1* | 2/2004 | Polansky | ............. | A61K 48/005 435/456 |
| 2004/0115712 A1 | 6/2004 | Engel et al. | | |
| 2005/0053950 A1 | 3/2005 | Zudaire Ubani et al. | | |
| 2010/0233686 A1 | 9/2010 | Higuchi et al. | | |
| 2011/0151459 A1 | 6/2011 | Rothmann et al. | | |
| 2011/0294676 A1 | 12/2011 | Cawthon | | |
| 2012/0100526 A1 | 4/2012 | Czajka et al. | | |
| 2012/0214158 A1 | 8/2012 | Cobb | | |
| 2014/0206567 A1 | 7/2014 | Niwa et al. | | |
| 2014/0349295 A1 | 11/2014 | Hosaka et al. | | |

| | | | |
|---|---|---|---|
| 2015/0132752 A1 | 5/2015 | Makino | |
| 2018/0087106 A1 | 3/2018 | Shimizu | |
| 2018/0155764 A1 | 6/2018 | Nagano | |

FOREIGN PATENT DOCUMENTS

| | | |
|---|---|---|
| CN | 101624629 | 1/2010 |
| EP | 1 411 133 | 4/2004 |
| EP | 2 116 614 | 11/2009 |
| EP | 2 143 742 | 1/2010 |
| EP | 2 787 077 | 10/2014 |
| JP | 2002-136300 | 5/2002 |
| JP | 2004-203 | 1/2004 |
| JP | 2008-173127 | 7/2008 |
| JP | 4724380 | 7/2011 |
| JP | 2012-513215 | 6/2012 |

(Continued)

OTHER PUBLICATIONS

Isegawa et al., PCR with quenching probes enables the rapid detection and identification of ganciclovir-resistance-causing U69 gene mutations in human herpesvirus 6. Mol Cell Probes. Aug. 2010; 24(4):167-77. Epub Jan. 18, 2010. (Year: 2010).*
Ieven et al., 1996. Detection of Mycoplasma pneumoniae by two polymerase chain reactions and role of *M. pneumoniae* in acute respiratory tract infections in pediatric patients. Journal of infectious diseases, 173(6), pp. 1445-1452. (Year: 1996).*
Lee YJ, Kim D, Lee K, Chun JY. Single-channel multiplexing without melting curve analysis in real-time PCR. Sci Rep. Dec. 11, 2014; 4:7439 pp. 1-6. (Year: 2014).*
Office Action issued Jul. 11, 2022 in corresponding Mexican Patent Application No. MX/a/2017/015673, with English Translation, 8 pages.

(Continued)

*Primary Examiner* — Gary Benzion
*Assistant Examiner* — Olayinka A Oyeyemi
(74) *Attorney, Agent, or Firm* — Wenderoth, Lind & Ponack, L.L.P.

(57) ABSTRACT

Provided is a kit for detecting multiple target nucleic acids capable of simultaneously amplifying and detecting multiple genes by means of one reaction vessel containing one kind of reaction solution and one kind of labels. Solution may contain first target nucleic acid (10) and second target nucleic acid (20) each of which dissociates at denaturation temperature T0. The solution further contains: DNA polymerase (30); a first target's primer (13) at annealing temperature T1 bonding with first single strands derived from the first target nucleic acid; a second target's primer (23) at annealing temperature T1 bonding with second single strands derived from the second target nucleic acid; a first target's probe (15) at annealing temperature T1 bonding with the first single strands derived from the first target nucleic acid; and a second target's probe (25) at second target detection temperature T3 which is lower than the annealing temperature T1 and elongation temperature T2 bonding with the second single strands derived from the second target nucleic acid. A condition that: T0 is higher than T2; T2 is not lower than T1; and T1 is higher than T3 is satisfied.

7 Claims, 22 Drawing Sheets

Specification includes a Sequence Listing.

(56) References Cited

FOREIGN PATENT DOCUMENTS

| | | |
|---|---|---|
| JP | 2013-60 | 1/2013 |
| KR | 20100134139 | 12/2010 |
| KR | 20140091562 | 7/2014 |
| WO | 2010/068576 | 6/2010 |
| WO | 2012093262 | 7/2012 |

OTHER PUBLICATIONS

Al-Marzooq F, Imad MA, How SH, Kuan YC, "Development of multiplex real-time PCT for the rapid detection of five bacterial causes of community acquired pneumonia", Trop Biomed. Dec. 2011; 28(3):545056. (Year: 2011).

Kageyama, S., Hirayama, H., Moriyasu, S. and Minamihashi, A, "Genetic diagnosis of band 3 deficiency using a quenching probe (Q-Probe)-PCR assay in bovine embryos", Japanese Journal of Veterinary Research, Feb. 2015, 63(1), pp. 45-51. (Year: 2015).

Tani H, Miyata R, Ichikawa K, Morishita S, Kurata S, Nakamura K, Tsuneda S, Sekiguchi Y, Noda N, "Universal quenching probe system: flexible, specific, and cost-effective real-time polymerase chain reaction method", Anal Chem. Jul. 15, 2009; 81(14):5678-86. (Year: 2009).

Tani et al., "Supporting Information", pp. 1-4. Anal Chem. Jul. 15, 2009; 81(14):5678-85. (Year: 2009).

Leven, M., Ursi, D., Van Bever, H., Quint, W., H.G.M. and Goossens, H., 1996, "Detection of *Mycoplasma pneumoniae* by two polymerase chain reactions and role of *M. pneumoniae* in acute respiratory tract infections in pediatric patients", Journal of infectious diseases, 173(6), pp. 1445-1452. (Year: 1996).

Gullsby K, Storm M, Bondeson K., "Simultaneous detection of *Chlamydophila pneumoniae* and *Mycoplasma pneumoniae* by use of molecular beacons in a duplex real-time PCR", J Clin Microbiol. 2008; 46:727-31. (Year: 2003).

Ursi, D., C. Dirven, K. Loens, M. Leven, and H. Goossens, 2003, "Detection of *Mycoplasma pneumoniae* in respiratory tract samples by real-time PCR using an inhibition control", J. Microbiol. Method 55:149-153. (Year: 2003).

Lee YJ, Kim D, Lee K, Chun JY, "Single-channel multiplexing without melting curve analysis in real-time PCR", Sci Rep. Dec. 1, 20141; 4:7439 pp. 1-6. (Year: 2014).

Isegawa Y, Matsumoto C, Nishinaka K, Nakano K, Tanaka T, Sugimoto N, Ohshima A, "PCR with quenching probes enables the rapid detection and identification of ganciclovir-resistance-causing U69 gene mutations in human herpesvirus 6", Mol Cell Probes. Aug. 2010; 24(4):167-77. Epub Jan. 18, 2010 (Year: 2010).

Extended European Search Report issued Feb. 9, 2018 in corresponding European patent application No. 16802989.0.

Communication pursuant to Article 94(3) EPC issued May 22, 2019 in European Patent Application No. 16802989.0.

Notification of Reason for Refusal issued May 31, 2019 in Korean Patent Application No. 10-2017-7033935, with English Translation.

Office Action issued Dec. 17, 2018 in corresponding Singapore patent application No. 11201708920P, 1 page.

Written Opinion issued Nov. 29, 2018 in corresponding Singapore patent application No. 11201708920P, 7 pages.

International Search Report issued Aug. 16, 2016 in International Application No. PCT/JP2016/063831.

Lee, D.H., "TOCE: Innovative Technology for High Multiplex Real-time PCR", Seegene Bulletin, Jul. 2012, vol. 1, (pp. 5-10).

* cited by examiner positive reference  p I C M 5

T E

SEQUENCE LISTING

```
<160> NUMBER OF SEQ ID NOS: 11

<210> SEQ ID NO 1
<211> LENGTH: 21
<212> TYPE: DNA
<213> ORGANISM: Mycoplasma pneumoniae

<400> SEQUENCE: 1
gccaccctcg ggggcagtca g                                            21

<210> SEQ ID NO 2
<211> LENGTH: 22
<212> TYPE: DNA
<213> ORGANISM: Mycoplasma pneumoniae

<400> SEQUENCE: 2
gagtcgggat tccccgcgga gg                                           22

<210> SEQ ID NO 3
<211> LENGTH: 26
<212> TYPE: DNA
<213> ORGANISM: Mycoplasma pneumoniae

<400> SEQUENCE: 3
ccctcgacca agccaacctc cagctc                                       26

<210> SEQ ID NO 4
<211> LENGTH: 17
<212> TYPE: DNA
<213> ORGANISM: Artificial Sequence
<220> FEATURE:
<223> OTHER INFORMATION: random sequence

<400> SEQUENCE: 4
agtgggactc accaacc                                                 17

<210> SEQ ID NO 5
<211> LENGTH: 16
```

<212> TYPE: DNA
<213> ORGANISM: Artificial Sequence
<220> FEATURE:
<223> OTHER INFORMATION: random sequence

<400> SEQUENCE: 5
agtgggactc accaac                                                                       16

<210> SEQ ID NO 6
<211> LENGTH: 30
<212> TYPE: DNA
<213> ORGANISM: Chlamydia trachomatis

<400> SEQUENCE: 6
tgagcaccct aggcgtttgt actccgtcac                                                        30

<210> SEQ ID NO 7
<211> LENGTH: 36
<212> TYPE: DNA
<213> ORGANISM: Chlamydia trachomatis

<400> SEQUENCE: 7
gcactttcta caagagtaca tcggtcaacg aagagg                                                 36

<210> SEQ ID NO 8
<211> LENGTH: 25
<212> TYPE: DNA
<213> ORGANISM: Neisseria gonorrhoeae

<400> SEQUENCE: 8
gggcgtggtt gaactggcaa aaagc                                                             25

<210> SEQ ID NO 9
<211> LENGTH: 27
<212> TYPE: DNA
<213> ORGANISM: Neisseria gonorrhoeae

<400> SEQUENCE: 9
cagtgatttt ggcattggcg atattgg                                                           27

<210> SEQ ID NO 10
<211> LENGTH: 26
<212> TYPE: DNA
<213> ORGANISM: Chlamydia trachomatis

<400> SEQUENCE: 10
tgcgggcgat ttgccttaac cccacc                                                            26

<210> SEQ ID NO 11
<211> LENGTH: 25
<212> TYPE: DNA
<213> ORGANISM: Neisseria gonorrhoeae

<400> SEQUENCE: 11
ctaagcaaaa ttcgaggggg aaaac                                                             25

KIT FOR TOGETHER DETECTING MULTIPLE TARGET NUCLEIC ACIDS DIFFERING FROM EACH OTHER AND DETECTION METHOD USING THE SAME

BACKGROUND OF THE INVENTION

1. Field of the Invention

The present invention relates to a detection kit for improving the PCR method and further for measuring multiple target nucleic acids, and art related to the same.

2. Description of the Related Art

In genetic screening, it is necessary to measure multiple target nucleic acids in many cases.

For example, the multiple target nucleic acids may be: a first pair of influenza A viruses and influenza B viruses, a second pair of influenza and RSV/human metapneumovirus; a third pair of *Chlamydia trachomatis* and *Neisseria gonorrhoeae*, which may cause sexually transmitted diseases; a fourth pair of *Mycoplasma pneumoniae* and resistance factor thereof; and so on.

Regarding the multiple target nucleic acids in some pairs of the above, the conditions of patients are similar to each other and also infection of the same expands simultaneously. So, it is conceivable to distinguish the multiple target nucleic acids from each other to make a diagnosis, thereby deciding on a course of treatment.

Considering the resistance factor is effective for selecting/judging medication against thereto, or the like.

As for only one measurement item, it is also helpful to set up internal control composition as means for confirming whether or not the measurement itself has been well done.

This is performed by: beforehand preparing a nucleic acid sequence to be amplified, the sequence not concerning a target gene of a detection object; and enabling to confirm whether or not the reaction has been well processed notwithstanding the existence or nonexistence of the target nucleic gene.

In this way, whether or not whether the reagent and the device for the measurement have acted effectively can be checked within the measurement system.

As mentioned above, in order to detect the multiple target nucleic acids, a first process of performing independent measurement for each of the multiple target nucleic acids, respectively, and a second process of distinguishing the multiple target nucleic acids from each other by means of different pilot dyes or the like, respectively can be conceived.

Alternatively, it is also possible to carry out the melting curve analysis method after having simultaneously processed amplification reaction. In this method after the amplification reaction, temperature is gradually increased/decreased to make distinction and judgment with respect to the multiple target nucleic acids based on both of first temperature wherein a change rate of fluorescent signals shows a peak and second temperature wherein the target nucleic acid is melt (the melting curve analysis method).

The first process of performing the independent measurement requires long time and high costs. The second process of distinguishing different labeling substances from each other costs too much because the second process needs not only preparing plural kinds of labeled reagents but also complicated wavelength-setting in an analyzer.

A case by means of the melting curve analysis method costs less than the above. However, since the temperature must be gradually changed, it is necessary to take about 5 to 10 minutes for changing the temperature in order to conduct precise analysis.

Reference 1 (Japanese application Laid-open No. 2002-136300) discloses: preparing a plurality of reaction vessels containing different reaction solution from each other, and performing amplification and detection with the plurality of reaction vessels, respectively.

So, reagent preparation and dispensing operations must be conducted for every item of the plurality of reaction vessels. There is a problem that it requires a long time.

Reference 2 (Japanese application Laid-open No. 2004-203) discloses simultaneously amplifying multiple genes by means of one reaction vessel containing one kind of reaction solution.

Distinction is carried out by using different pilot dyes for each of the multiple genes. So, a plurality of optical systems installed in an analyzer are needed as many as the used pilot dyes. In other words, the analyzer costs too much. This is a serious problem.

Reference 3 (Japanese application Laid-open No. 2008-173127) discloses simultaneously amplifying multiple genes by means of one reaction vessel containing one kind of reaction solution.

Dissociation temperature of PCR products and labeled probes should be changed for every gene. After amplification, while temperature is gradually increased from a lower temperature side to a higher temperature side, dissociation curve analysis, which is a synonym of "melting curve analysis", of monitoring fluorescence values is carried out. Distinction is carried out by monitoring existence or nonexistence of a peak depending on base sequence at the respective dissociation temperature.

If temperature is changed speedily upon the melting curve analysis, it becomes difficult to identify melting temperature for each gene. Accordingly, there is a problem that extra time of about 5 to 10 minutes after PCR is required.

Reference 4 (Japanese unexamined patent application publication <Translation of PCT application> No. 2012-513215) discloses simultaneously amplifying multiple genes by means of one reaction vessel.

Dissociation temperature of PCR products and melting temperature of primers are changed for every gene. Distinction is carried out by monitoring fluorescence at the respective melting temperature.

In an ordinary PCR profile, one cycle includes: a denaturation step; and an annealing and elongation step. In Reference 4, the melting temperature of PCR products is changed for every gene. Accordingly, too many conditions should be taken into consideration, design of the profile is also difficult, and time for measurement must be too long.

Furthermore, there is another problem that temperature must be drastically changed to task the device.

LIST OF CITED REFERENCES

Reference 1: Japanese application Laid-open No. 2(02-136300;

Reference 2: Japanese application Laid-open No. 2004-203;

Reference 3: Japanese application Laid-open No. 2008-173127;

Reference 4: Japanese unexamined patent application publication (Translation of PCT application) No. 2012-513215; and Reference 5: Japanese registered patent No. 4724380.

OBJECTS AND SUMMARY OF THE INVENTION

In view of the above, an object of the present invention is to provide a kit for detecting multiple target nucleic acids capable of simultaneously amplifying and detecting multiple genes by means of one reaction vessel containing one kind of reaction solution and one label.

A first aspect of the present invention provides a kit for together detecting multiple target nucleic acids differing from each other, comprising: solution, the multiple target nucleic acids including a first target nucleic acid and a second target nucleic acid; defining: T0 as denaturation temperature: T1 as annealing temperature; T2 as elongation temperature; and T3 as second target detection temperature, T0 through T3 being set up such that a condition that: T0 is higher than T2: T2 is not lower than T1; and T1 is higher than T3 is satisfied, the solution being capable of containing the first target nucleic acid and the second target nucleic acid therein, at the denaturation temperature T0, first double-stranded hydrogen bond of the first target nucleic acid being cut off to be dissociate into first two single strands, second double-stranded hydrogen bond of the second target nucleic acid being cut off to be dissociate into second two single strands, respectively, the solution further containing therein: a first target's primer at the annealing temperature T1 specifically bonding with either of the first two single strands into which the first target nucleic acid has been dissociated: a second target's primer at the annealing temperature T1 specifically bonding with either of the second two single strands into which the second target nucleic acid has been dissociated; a first target's probe at the annealing temperature T1 specifically bonding with either of the first two single strands into which the first target nucleic acid has been dissociated, the first target's probe including a first labeling substance changing first fluorescent signals thereof when the first target's probe specifically bonds with either of the first two single strands: DNA polymerase; deoxyribonucleoside triphoshate at the elongation temperature T2 bonding by action of the DNA polymerase with both of the first two single strands into which the first target nucleic acid has been dissociated and the second two single strands into which the second target nucleic acid has been dissociated; and a second target's probe at the annealing temperature T1 bonding with neither the first two single strands into which the first target nucleic acid has been dissociated nor the second two single strands into which the second target nucleic acid has been dissociated, the second target's probe at the second target detection temperature T3 bonding with the second two single strands into which the second target nucleic acid has been dissociated, the second target's probe including a second labeling substance changing second fluorescent signals thereof when the second target's probe specifically bonds with either of the second two single strands.

It is preferable that each of the first labeling substance and the second labeling substance is selected from a group consisting of: a QProbe (registered trademark) probe; an Eprobe (registered trademark) probe; and a TaqMan (registered trademark) probe.

The fluorescent signals may be shown by quenching light when the annealing occurs. Alternatively, the fluorescent signals may be shown by emitting light when the annealing occurs.

It is preferable that the first target nucleic acid is at least one of a *Mycoplasma pneumoniae* P1 gene and a *Chlamydia trachomatis* endogeneous plasmid gene, and the second target nucleic acid is at least one of internal control composition and a *Neisseria gonorrhoeae* CMT gene, respectively.

Effect of Invention

As mentioned above, according to the present invention, the multiple target nucleic acids can be detected by means of one kind of mixed-solution and one kind of labeling substances.

Distinction of the multiple target nucleic acids can be carried out without melting curve analysis. Accordingly, measuring time can be remarkably shortened, thereby providing excellent practical performance.

DETAILED DESCRIPTION OF THE PREFERRED EMBODIMENTS

The present inventors have developed a kit for detecting nucleic acids by means of one kind of fluorescent labels and one reaction vessel containing one kind of reaction solution. Condition setting with respect to annealing temperature of probes and temperature change profiles in the PCR method has been incorporated within the present kit.

As shown in FIG. 35, the present kit uses four kinds of temperature including: denaturation temperature T0 (95 Centigrade); annealing temperature T1 (70 Centigrade); elongation temperature T2 (72 Centigrade), and second target detection temperature T3 (55 Centigrade).

The four kinds of temperature are set up such that a condition that T0>T2>=T1>T3 is satisfied.

Of course, the above temperature vales are mere examples, and may be variously changed as mentioned later.

Herein, the multiple target nucleic acids are a first target nucleic acid and a second target nucleic acid. However if needed, a third target nucleic acid or more can be added thereto by adding further setting such as third target detection temperature T4 (T3>T4), or the like.

Referring now to FIG. 36, elements of the present kit will now be explained.

First, in the present kit, it is assumed that a first target nucleic acid 10 and a second target nucleic acid 20 are targets to be detected.

Hereinafter for the simplicity of explanation, only a case where both of the first target nucleic acid 10 and the second target nucleic acid 20 are contained in solution 2 within a vessel 1, that is, a case of positive and positive will be explained below. Details of the solution 2 will be mentioned later.

Needless to say, in another case where at least one target is negative, the solution 2 does not contain the at least one of the first target nucleic acid 10 and the second target nucleic acid 20. Therefore, fluorescent signals and amplification regarding the not contained target nucleic acid will not be carried out in the following explanation.

As shown in FIG. 37 (*a*), when temperature of the solution 2 is increased to reach the denaturation temperature T0, hydrogen bonds of double strands of the first target nucleic acid 10 and the second target nucleic acid 20 are respectively cut off to be dissociated into respective first and second two single strands (from the first target nucleic acid 10 to a first single strand 11 and a second single strand 12, from second target nucleic acid 20 to a first single strand 21 and a second single strand 22).

As shown in FIG. 37 (*b*), the temperature is decreased from the denaturation temperature T0 to reach the annealing temperature T1, regarding the first target nucleic acid 10, a first target's F-primer 13 specifically bonds with a complementary sequence of the first single strand 11, and a first target's R-primer 14 specifically bonds with another complementary sequence of the second single strand 12, respectively.

Furthermore, similar to the above, regarding the second target nucleic acid 20, a second target's F-primer 23 specifically bonds with a complementary sequence of the first single strand 21, and a second target's R-primer 24 specifically bonds with another complementary sequence of the second single strand 22, respectively.

At the annealing temperature T1 shown in FIG. 37 (*b*), the first target's probe 15 labeled by means of the first labeling substance 16 specifically bonds with a specific part of the first single strand 11 derived from the first target nucleic acid 10, thereby the first labeling substance 16 outputs first fluorescence signals.

On the other hand, the annealing temperature T1 is higher than the second target detection temperature T3. For this reason, the second target's probe 25 labeled by means of the second labeling substance 26 does not bond with the first single strand 21 derived from the second target nucleic acid 20, thereby the second labeling substance 26 outputs no fluorescence signal at this time.

As shown in FIG. 37 (*c*), when the temperature is increased from the annealing temperature T1 to the elongation temperature T2, amplification reaction progresses advances as follows. This is because the solution 2 contains an amount sufficient for repeating PCR cycles of DNA polymerase 30 and deoxyribonucleoside triphoshate 31.

Regarding the first target nucleic acid 10, from the first target's F-primer 13 bonding with the first single strand 11, and from the first target's R-primer 14 bonding with the second single strand 12, the deoxyribonucleoside triphoshate 31 bonds therewith to elongate, respectively.

Regarding the second target nucleic acid 20, from the second target's F-primer 23 bonding with the first single strand 21, and from the second target's R-primer 24 bonding with the second single strand 22, the deoxyribonucleoside triphoshate 31 bonds therewith to elongate, respectively.

As clear comparing FIG. 37 (*d*) with FIG. 36, upon the amplification reaction has been completed, both of the first target nucleic acid 10 and the second target nucleic acid 20 have been doubled.

Returning to a step shown in FIG. 37 (*a*) again to repeat the above steps of FIG. 37 (*a*) through FIG. 37 (*d*) enables to repeat the amplification reaction and changes of fluorescent signals by means of the first labeling substance 16.

Next referring now to FIG. 38, a case where the temperature is decreased from the denaturation temperature T0 to the second target detection temperature T3 will now be explained.

As shown in FIG. 38 (*a*), at the denaturation temperature T0, the situation is the same as that of FIG. 37 (*a*).

However, upon the temperature is decreased to reach the second target temperature detection temperature T3, the situation is as shown in FIG. 38 (*b*) differing from FIG. 37 (*b*).

Namely, as shown in FIG. 38 (*b*), the first target's probe 15 labeled by the first labeling substance 16 specifically bonds with a specific part of the first single strand 11 derived from the first target nucleic acid 10, and the first fluorescent signals of the first labeling substance 16 change. This is the same as that of FIG. 37 (*b*).

However, the temperature is the second target detection temperature T3. Accordingly, also the second target's probe 25 labeled by the second labeling substance 26 bonds with the first single strand 21 derived from the second target nucleic acid 20, and the second fluorescent signals of the second labeling substance 26 also change.

Herein, it is preferable that the first labeling substance 16 and the second labeling substance 26 are identical.

As a result, capturing the difference caused by the changes of the first and second fluorescent signals according to the second labeling substance 26 enables to judge the existence or nonexistence (positivity/negativity) of the second target nucleic acid 20.

In addition as clear from the above-mentioned, it may be understood that the multiple target nucleic acids can be respectively detected during a series of continuing steps by means of the reaction vessel containing one kind of reaction solution.

Hereinafter, Embodiments of detecting multiple nucleic acids by means of three kinds of probes will now be explained more concretely. In the Embodiments, the QProbe (registered trademark) method, the Eprobe (registered trademark) method, and the TaqMan (registered trademark) method have been used.

Necessary information for operation including: primer sequences, base sequences of the respective Eprobes; and material of nucleic acid samples will be also shown.

Embodiment 1

<Detection of *Mycoplasma pneumoniae* P1 Genes and Internal Control Composition According to the QProbe Method>

Detection of *Mycoplasma pneumoniae* P1 genes and internal control composition according to the QProbe method has been performed.

<Material and Steps>

(Primer)

A pair of primers used for the PCR method in Embodiment 1 are as shown in Table 1.

TABLE 1

| Primers used for PCR in this Embodiment | | |
| --- | --- | --- |
| Primer name | Sequence (5'→3') | Length (bp) |
| MYC F | GCCACCCTCGGGGGCAGTCAG (SEQ ID No. 1) | 21 |
| MYC F | GAGTCGGGATTCCCCGCGGAGG (SEQ ID No. 2) | 22 |

As sequence No. 1 and sequence No. 2, (primer pair for P1 adhesin gene) sequences recited in the report (The Journal Of Infectious Diseases, 1996: 173; 1445-52) by Ieven et al. have been used.

(Nucleic Acid Sample)

Nucleic acid samples used for the PCR method in Embodiment 1 are shown below.

(pMYC)

*Mycoplasma pneumoniae* is a pathogenic organism of *Mycoplasma* pneumonia. P1 protein is membrane protein derived from *Mycoplasma pneumoniae*. Gene fragments (sequences amplified by a pair of primers of SEQ ID NO: 1 and SEQ ID NO: 2) encode the P1 protein. pMYC is a plasmid DNA produced by artificial synthesizing the gene fragments to be incorporated into a pMD20T vector. Production of the plasmid DNA has been performed by requesting custom synthesis to the Takara Bio Inc.

(pICM5)

7

In order to be capable of amplifying pICM5 plasmid by means of common primers of the pair of primers of SEQ ID NO: 1 and SEQ ID NO: 2, pICM5 is a plasmid DNA produced by artificial synthesizing a sequence including a complementary sequence to the pair of the primers to be incorporated into a pMD20T vector. Production of the plasmid DNA has been performed by requesting custom synthesis to the Takara Bio Inc.

(Preparation of Nucleic Acid Sample)

First length of the pMYC plasmid is 2942 [bp], and second length of the pICM5 plasmid is 2886 [bp].

Based on the first and second length and the concentration [μg/μl] of plasmid solution, the number of copies per 1 [μl] has been calculated. After that, by means of TE buffer solution (10 [mM] Tris-HCl, 1.0 [mM] EDTA pH: 8.0), the pMYC plasmid has been diluted to be $1 \times 10^5$ [copies/μl], and the pICM5 plasmid has been diluted to be $1 \times 10^3$ [copies/μl], respectively.

(Probe)

Information of the Eprobe used for the PCR method in Embodiment 1 is as shown in Table 2.

TABLE 2

Probes used for PCR in this Embodiment

| Probe name | Sequence (5'→3') | Length (bp) |
|---|---|---|
| MYC QP | CCCTCGACCAAGCCAACCTCCAGCTC (SEQ ID No. 3) | 26 |
| IC QP | AGTGGGACTCACCAACC (SEQ ID No. 4) | 17 |

Based on a basic sequence of PCR products capable of being amplified by means of the pair of primers in Table 1, a specific region for SEQ ID NO: 3 and SEQ ID NO: 4 has been selected referring to Tm values calculated with a QProbe design support tool on the J-Bio21 Center home pages.

"MYC QP" is one QProbe specifically annealing the pMYC plasmid, and "IC QP" is another QProbe specifically annealing the pICM5 plasmid. As fluorescent dye for both of "MYC QP" and "IC QP", "BODIPY FL" (registered trademark) has been used to label "C" at 3' ends, respectively. Production of the QProbes has been performed by requesting custom synthesis to the NIPPON STEEL & SUMIKIN Eco-Tech Corporation.

(Conditions of PCR and Fluorescence Measurement)

In Embodiment 1, among two kinds of target nucleic acids to be amplified within one vessel containing one kind of reaction liquid, a first Tm value for "MYC QP" that is the QProbe specifically annealing the pMYC plasmid of the first target is set up to be higher than another Tm value for the primers to perform first detection during amplification reaction.

In addition, a second Tm value for "IC QP" that is the QProbe specifically annealing the pICM5 plasmid of the second target is set up to be lower than changes (70 Centigrade to 95 Centigrade) of temperature during the amplification reaction to perform second detection after the amplification reaction.

Table 3 and Table 4 show composition of the PCR reaction solution and the reaction conditions respectively, and FIG. 1 shows a graph of the changes of temperature of the mixed solution.

8

TABLE 3

Composition of PCR solution in QProbe method

| Solution composition | Final concentration |
|---|---|
| MilliQ(TM) water | — |
| PCR buffer | ×1 |
| dNTP Mix | 150 μM |
| MYC F | 0.20 μM |
| MYC R | 0.60 μM |
| MYC QP | 0.15 μM |
| IC QP | 0.15 μM |
| KOD exo (−) DNA Polymerase | 0.0125 U/μl |
| Target nucleic acid | — |

The above has been prepared to be 20 μL

TABLE 4

Reaction conditions in QProbe method

| Reaction steps | Temperature(° C.) | | Time(s) |
|---|---|---|---|
| Initial denaturation | 95 | $T_0$ | 120 |
| Amplification | 95 | $T_0$ | 10 (FL measurement) |
| (1-44 cycles) | 70 | $T_1$ | 10 |
| | 72 | $T_2$ | 10 (FL measurement) |
| Second target | 95 | $T_0$ | 10 (FL measurement) |
| NA detecting | 55 | $T_3$ | 10 (FL measurement) |

For the PCR and the fluorescence measurement, "Light Cycler nano system" (registered trademark of the Roche Diagnostics K.K.) has been used.

The combination of 510 to 528 [nm] has been selected for excitation wavelength and fluorescent wavelength upon fluorescence measurement. Fluorescence values have been measured at the denaturation step (95 Centigrade) and the elongation step (72 Centigrade) for every cycle. Furthermore, after the amplification reaction has been completed, at a step for detecting the second target (95 Centigrade and 55 Centigrade), fluorescence measurement has been performed.

FIG. 2 shows fluorescent measurement conditions at the final cycle of the amplification reaction and at the second target detection step.

(how to Process Data)

Analysis software provided with the Light Cycler nano system does not support an analysis method of using the QProbes. Accordingly, correction calculation has been performed on obtained raw data as follows, referring to a method disclosed in Reference 5 (Japanese registered patent No. 4724380).

For every cycle of the amplification reaction and the second target detection step, calculation has been carried out according to the following formulae.

$$fn = fhyb.n/fden.n \qquad \text{(Formula 1)}$$

$$fe = fhyb.e/fden.e \qquad \text{(Formula 1')}$$

herein, fn: fluorescence intensity value in n cycle calculated according to Formula 1;

fhyb.n: fluorescence intensity value at the elongation step in n-th cycle;

fden.n: fluorescence intensity value at the denaturation step in n-th cycle;

fe: fluorescence intensity value at the second target detection step calculated according to Formula 1';

fhyb.e: fluorescence intensity value (55 Centigrade) at the second target detection step; and fden.e: fluorescence intensity value (95 Centigrade) at the second target detection step.

Next, for every cycle of the amplification reaction and the second target detection step, calculation has been carried out according to the following formulae.

$$Fn = fn/f10 \quad \text{(Formula 2)}$$

$$Fe = fe/f10 \quad \text{(Formula 2')}$$

herein,

Fn: relative value in n-th cycle assuming that the fluorescence intensity value in the tenth cycle obtained according to Formula 1 is equal to a value of "1", and Fe: relative value at the second target detection step assuming that the fluorescence intensity value in the tenth cycle obtained according to Formula 1' is equal to a value of "1".

F44 which is a value of Fn at the final cycle of the amplification reaction has been used for judgment of the existence or nonexistence of the first target nucleic acid.

Further calculation has been carried out according to the following formula.

$$Fs = Fe - F44 \quad \text{(Formula 3)}$$

herein,

Fs: measured value regarding the second target.

The value of Fs has been used for determination of the existence or nonexistence of the second target nucleic acid.

Determination according to the QProbe method has been performed using the method shown below.

The F44 value of the measurement sample has been compared with Threshold 1. And, when the F44 value of the measurement sample is lower than Threshold 1, it has been determined that the first target nucleic acid is positive (existence), otherwise negative (nonexistence).

As Threshold 1, an average of F44 values of the negative reference (reagent TE buffer added thereto instead of DNA) minus three times the standard deviation (hereinafter, called as "mean−3SD") has been used.

Notwithstanding the first target nucleic acid is positive or negative, the Fs value has been compared with Threshold 2, and when the Fs value is lower than Threshold 2 it has been determined that the second target nucleic acid is positive (existence), otherwise negative (nonexistence).

As Threshold 2, the value of "mean−3SD" of a sample to which only the pMYC plasmid is added has been used. FIG. 3 shows a flow chart of the determination method related thereto.

As nucleic acid samples, the pMYC plasmid has been used for *Mycoplasma pneumoniae* P1 genes, the pICM5 plasmid has been used for the internal control composition, and the PCR has been performed thereon.

A first Tm value of 72.5 Centigrade has been set for a sequence of MYC QP, and a second Tm value of 57.5 Centigrade has been set for a sequence of IC QP. For this reason, it has been estimated that probes anneal only MYC QP during the temperature range (from 70 Centigrade to 95 Centigrade) in the PCR.

Since the fluorescence measurement with respect to the second target detection step has been carried out at 95 Centigrade and 55 Centigrade which is lower than the Tm value of IC QP, it has been estimated that extinction of both of MYC QP and the IC QP has been simultaneously detected according to measured values at the second target detection step.

Regarding an amplification curve of the negative reference, extinction has not observed until 44 cycles when the PCR ends. This is because a value 0.998 of F44 is not lower than a value 0.997 of Threshold 1. At this time, "mean−3SD" is equal to 0.997 to be regarded as Threshold 1 for the first target detection in Embodiment 1, thereby being shown in Table 5. The amplification curve related thereto is also shown in FIG. 4.

Regarding another amplification curve of the pMYC plasmid of the first target nucleic acid, extinction caused by annealing of MYC QP has been observed from about 28 cycles.

It has been revealed that a value 0.913 of F44 has been lower than Threshold 1, and further that a first objective region of the pMYC plasmid has been amplified. At this time, "mean−3SD" of Fs has been equal to −0.056 to be regarded as Threshold 2 for the second target detection, thereby being shown in Table 5. The amplification curve related thereto is also shown in FIG. 5.

Regarding an amplification curve of the pICM5 plasmid of the second target nucleic acid, no extinction has been observed during the amplification reaction. This is because a value 0.997 of F44 is not lower than a value 0.997 of Threshold 1. A value −0.118 of Fs has been lower than Threshold 2.

The above-mentioned results have revealed that the objective region of the pMYC plasmid has been not amplified, further that the objective region of the pICM5 plasmid has been amplified.

Table 5 shows the value of the Fs. The amplification curve is shown in FIG. 6.

TABLE 5

| Values used for determination in QProbe method | | | | |
|---|---|---|---|---|
| | TE | pMYC | pICM5 | pMYC pICM5 |
| F44 | 0.998 | 0.913 | 0.997 | 0.912 |
| F44 (Average − 3SD) | 0.997 ※1 | — | — | — |
| Fe | 0.971 | 0.862 | 0.879 | 0.796 |
| Fs | −0.027 | −0.051 | −0.118 | −0.116 |
| Fs (Average − 3SD) | — | −0.056 ※2 | — | — |

※1 Threshold 1
※2 Threshold 2

Regarding an amplification curve upon both the pMYC plasmid of the first target nucleic acid and the pICM5 plasmid of the second target nucleic acid have been added to the solution, extinction caused by annealing of MYC QP has been observed from about 28 cycles as the same as the above-mentioned amplification curve of the pMYC plasmid. A value 0.912 of F44 has been lower than Threshold 1, and it has been revealed that the objective region of the pMYC plasmid has been amplified.

The value −0.116 of Fs is lower than Threshold 2, and it has been revealed that the objective region of the pICM5 plasmid has been amplified. Table 5 shows the value of the Fs. The amplification curve related thereto is shown in FIG. 7.

After the PCR has been completed, agarose electrophoresis has been performed onto these PCR products. First objective PCR products with respect to the pMYC plasmid-added sample have been confirmed at near 206 [bp], and second objective PCR products with respect to the pICM5 plasmid-added sample have been confirmed at near 150 [bp].

According to the above-mentioned results, it has been revealed that *Mycoplasma pneumoniae* P1 genes and internal control composition can be detected by means of one reaction vessel containing one kind of reaction solution and one kind of fluorescent labels when the method of designing probes and temperature profiles are incorporated with the QProbe method.

Embodiment 2

<Detection of *Mycoplasma Pneumoniae* P1 Genes and Internal Control Composition Based on QProbe Method while Changing Profile at Second Detection Step>

According to a method of changing the profiles at the second detection step in Embodiment 1, *Mycoplasma pneumoniae* P1 genes and internal control composition have been detected based on the QProbe method.

The primers, probes, reaction solution composition, and nucleic acids have been used for the PCR method as the same as Embodiment 1. Table 6 shows reaction conditions in Embodiment 2.

TABLE 6

Reaction conditions after profile at second
NA target detecting step is changed

| Reaction steps | Temperature (° C.) | | Time(s) |
|---|---|---|---|
| Initial denaturation | 95 | $T_0$ | 120 |
| Amplification | 95 | $T_0$ | 10 (FL measurement) |
| (1-44 cycles) | 70 | $T_1$ | 10 |
| | 72 | $T_2$ | 10 (FL measurement) |
| Second target NA detecting | 55 | $T_3$ | 10 (FL measurement) |

At the second target detection step in Embodiment 2, fluorescence measurement has been conducted at 55 Centigrade. FIG. 8 shows fluorescent measurement conditions at the final cycle of the amplification reaction and at the second target detection step.

In Embodiment 2, fe has been calculated as follows. Calculation other than fe has been carried out as the same as Embodiment 1.

$$fe = fhyb.e/fden.44$$

herein, fe: fluorescence intensity value at the second target detection step;

fhyb.e: fluorescence intensity value (55 Centigrade) at the second target detection step;

fden.44: fluorescence intensity value (95 Centigrade) at the final cycle of amplification reaction.

Determination in Embodiment 2 has been performed as below.

The F44 value of the measurement sample has been compared with Threshold 3. And, when the F44 value of the measurement sample is lower than Threshold 3, it has been determined that the first target nucleic acid is positive (existence), otherwise negative (nonexistence).

As Threshold 3, an average of F44 values of the negative reference minus three times the standard deviation (hereinafter, called as "mean−3SD") has been used.

Notwithstanding the first target nucleic acid is positive or negative, the Fs value has been compared with Threshold 4, and when the Fs value is lower than Threshold 4 it has been determined that the second target nucleic acid is positive (existence), otherwise negative (nonexistence).

As Threshold 4, the value of "mean−3SD" of a sample to which only the pMYC plasmid is added has been used.

Regarding an amplification curve of the negative reference, extinction has not observed until 44 cycles when the PCR ends. This is because a value 0.998 of F44 is not lower than a value 0.997 of Threshold 3. At this time, "mean−3SD" is equal to 0.997 to be regarded as Threshold 3 for the first target detection in this Embodiment, thereby being shown in Table 7. The amplification curve related thereto is also shown in FIG. 9.

Regarding another amplification curve of the pMYC plasmid of the first target nucleic acid, extinction caused by annealing of MYC QP has been observed from about 28 cycles. It has been revealed that a value 0.912 of F44 has been lower than Threshold 3, and further that the objective region of the pMYC plasmid has been amplified.

At this time, "mean−3SD" of Fs has been equal to −0.052 to be regarded as Threshold 4 for the second target detection, thereby being shown in Table 7. The amplification curve related thereto is also shown in FIG. 10.

Regarding an amplification curve of the pICM5 plasmid, no extinction has been observed during the amplification reaction. This is because a value 0.997 of F44 is not lower than a value 0.997 of Threshold 3. A value −0.170 of Fs has been lower than Threshold 4.

The above-mentioned results have revealed that the objective region of the pMYC plasmid has been not amplified, further that the objective region of the pICM5 plasmid has been amplified. Table 7 shows the value of Fs. The amplification curve is shown in FIG. 11.

TABLE 7

Values used for determination in QProbe method
after profile at second NA target detecting step is changed

| | TE | | pMYC | pICM5 | pMYC pICM5 |
|---|---|---|---|---|---|
| F44 | 0.998 | | 0.912 | 0.997 | 0.911 |
| F44 (Average − 3SD) | 0.997 | ※1 | — | — | — |
| Fe | 0.961 | | 0.869 | 0.827 | 0.797 |
| Fs | −0.037 | | −0.043 | −0.170 | −0.114 |
| Fs (Average − 3SD) | — | | −0.052 ※2 | — | — |

※1 Threshold 3
※2 Threshold 4

Regarding an amplification curve upon both the pMYC plasmid of the first target nucleic acid and the pICM5 plasmid of the second target nucleic acid have been added to the solution as the above-mentioned amplification curve of the pMYC plasmid, extinction caused by annealing of MYC QP has been observed from about 28 cycles. A value 0.911 of F 44 has been lower than Threshold 3, and it has been revealed that the objective region of the pMYC plasmid has been amplified.

The value −0.114 of Fs is lower than Threshold 4, and it has been revealed that the objective region of the pICM5 plasmid has been amplified. Table 7 shows the value of the Fs. The amplification curve related thereto is shown in FIG. 12.

According to the above results, it has been revealed that upon using the fluorescence intensity value (95 Centigrade) at the final cycle of the amplification reaction (fden.44) the second target can be detected.

Embodiment 3

\<Detection of *Mycoplasma pneumoniae* P1 Genes and Internal Control Composition Based on Eprobe Method\>

*Mycoplasma pneumoniae* Pt genes and internal control composition have been detected based on the Eprobe method.

The same primers and nucleic acid samples for PCR as Embodiment 1 have been used. Table 8 shows probe information used for the PCR in Embodiment 3.

TABLE 8

| Probes used for PCR in this Embodiment | | |
|---|---|---|
| Probe name | Sequence (5'→3') | Length (bp) |
| MYC EP | CCCTCGACCAAGCCAACCTCCAGCTC (SEQ ID No. 3) | 26 |
| IC EP | AGTGGGACTCACCAAC (SEQ ID No. 5) | 16 |

A specific region for Eprobe has been selected referring to Tm values calculated by means of "Edesign" software produced by the K. K. Dnaform.

"MYC EP" is one Eprobe specifically annealing the pMYC plasmid, and "IC EP" is another Eprobe specifically annealing the pICM5 plasmid. As fluorescent dye for both of "MYC EP" and "IC EP", "D514" has been used. The nineteenth "T" from 5' end of "MYC EP" and the ninth "T" from 5' end of "IC EP" have been labeled, respectively.

Production of the Eprobes has been performed by requesting custom synthesis to the Eurofins Genomics K.K. The PCR reaction solution composition and the reaction conditions are shown in Table 9 and Table 10.

TABLE 9

| Composition of PCR solution in EProbe method | |
|---|---|
| Solution composition | Final concentration |
| MilliQ(TM) water | — |
| PCR buffer | ×1 |
| dNTP Mix | 150 µM |
| MYC F | 0.20 µM |
| MYCR | 0.80 µM |
| MYC EP | 0.40 µM |
| IC EP | 0.40 µM |
| KOD exo (—) DNA Polymerase | 0.0125 U/µl |
| Target nucleic acid | |

The above has been prepared to be 20 µL.

TABLE 10

| Reaction conditions in EProbe method | | | |
|---|---|---|---|
| Reaction steps | Temperature (° C.) | | Time(s) |
| Initial denaturation | 95 | $T_0$ | 120 |
| Amplification | 95 | $T_0$ | 10 (FL measurement) |
| (1-40 cycles) | 70 | $T_1$ | 10 |
| | 72 | $T_2$ | 10 (FL measurement) |

TABLE 10-continued

| Reaction conditions in EProbe method | | | |
|---|---|---|---|
| Reaction steps | Temperature (° C.) | | Time(s) |
| Second target NA detecting | 95 | $T_0$ | 10 (FL measurement) |
| | 55 | $T_3$ | 10 (FL measurement) |

The combination of 530 to 548 [nm] has been selected for excitation wavelength and fluorescent wavelength upon fluorescence measurement.

Fs in Embodiment 3 has been calculated with the following Formula. The other calculations have been carried out as the same as Embodiment 1.

$$Fs = Fe - F40$$

Determination in Embodiment 3 has been performed using the method shown below. The F40 value of the measurement sample has been compared with Threshold 5. And, when the F40 value of the measurement sample is higher than Threshold 5, it has been determined that the first target nucleic acid is positive (existence), otherwise negative (nonexistence).

As Threshold 5, an average of F40 values of the negative reference plus three times the standard deviation (hereinafter, called as "mean+3SD") has been used.

Notwithstanding the first target nucleic acid is positive or negative, the Fs value has been compared with Threshold 6, and when the Fs value is higher than Threshold 6, it has been determined that the second target nucleic acid is positive (existence), otherwise negative (nonexistence).

As Threshold 6, the value of "mean+3SD" of a sample to which only the pMYC plasmid is added has been used. FIG. 13 shows a flow chart of the determination method related thereto.

A first Tm value of 76.4 Centigrade has been set for a sequence of MYC EP, and a second Tm value of 59.8 Centigrade has been set for a sequence of IC EP. For this reason, it has been estimated that probes anneal only MYC EP during the temperature range (from 70 Centigrade to 95 Centigrade) in the PCR.

Since the fluorescence measurement with respect to the second target detection step has been carried out at 95 Centigrade and 55 Centigrade which is lower than the Tm value of IC EP, it has been estimated that emission of both of MYC EP and the IC EP has been simultaneously detected according to measured values at the second target detection step.

Regarding an amplification curve of the negative reference, emission has not observed until 40 cycles when the PCR ends. This is because a value 1.007 of F40 is not higher than a value 1.013 of Threshold 5. At this time, "mean+3SD" is equal to 1.013 to be regarded as Threshold 5 for the first target detection, thereby being shown in Table 11. The amplification curve related thereto is also shown in FIG. 14.

Regarding another amplification curve of the pMYC plasmid of the first target nucleic acid, emission caused by annealing of MYC EP has been observed from about 29 cycles. It has been revealed that a value 2.314 of F40 has been higher than Threshold 5, and further that the objective region of the pMYC plasmid has been amplified.

At this time, "mean+3SD" of Fs has been equal to 3.695 to be regarded as Threshold 6 for the second target detection, thereby being shown in Table 11. The amplification curve related thereto is also shown in FIG. 15.

Regarding an amplification curve of the pICM5 plasmid of the second target nucleic acid, no emission has been observed during the amplification reaction. This is because a value 1.012 of F40 is not higher than a value 1.013 of Threshold 5. A value 4.012 of Fs has been higher than Threshold 6.

The above-mentioned results have revealed that the objective region of the pMYC plasmid has been not amplified, further that the objective region of the pICM5 plasmid has been amplified. The value of Fs is shown in Table 11, and the amplification curve related thereto is also shown in FIG. 16.

TABLE 11

Values used for determination in EProbe method

| | TE | pMYC | pICM5 | pMYC pICM5 |
|---|---|---|---|---|
| F40 | 1.007 | 2.314 | 1.012 | 2.355 |
| F40 (Average + 3SD) | 1.013 ✕1 | — | — | — |
| Fe | 3.149 | 5.837 | 5.024 | 6.609 |
| Fs | 2.142 | 3.523 | 4.012 | 4.254 |
| Fs (Averag + 3SD) | — | 3.695 ✕2 | — | — |

✕1 Threshold 5
✕2 Threshold 6

Regarding an amplification curve upon both the pMYC plasmid of the first target nucleic acid and the pICM5 plasmid of the second target nucleic acid have been added to the solution, emission caused by annealing of MYC EP has been observed from about 29 cycles as the same as the above-mentioned amplification curve of the pMYC plasmid. A value 2.355 of F40 has been higher than Threshold 5, and it has been revealed that the objective region of the pMYC plasmid has been amplified.

A value 4.254 of Fs is higher than Threshold 6, and it has been revealed that the objective region of the pICM5 plasmid has been amplified. Table 11 shows the value of the Fs. The amplification curve related thereto is shown in FIG. 17.

According to the above-mentioned results, it has been revealed that *Mycoplasma pneumoniae* P1 genes and internal control composition can be detected by means of one reaction vessel containing one kind of reaction solution and one kind of fluorescent labels when the method of designing probes and temperature profiles are combined even with the Eprobe method.

Embodiment 4

<Detection of *Mycoplasma pneumoniae* P1 Genes and Internal Control Composition Based on TaqMan Probe Method>

According to the TaqMan probe method, *Mycoplasma pneumoniae* P1 genes and internal control composition have been detected. The primers and nucleic acid samples have been used for the PCR method as the same of Embodiment 1.

Table 12 shows information of the probes used for the PCR method in Embodiment 4.

TABLE 12

Probes used for PCR in this Embodiment

| Probe name | Sequence (5'→3') | Length (bp) |
|---|---|---|
| MYC Taq | CCCTCGACCAAGCCAACCTCCAGCTC (SEQ ID No. 3) | 26 |

TABLE 12-continued

Probes used for PCR in this Embodiment

| Probe name | Sequence (5'→3') | Length (bp) |
|---|---|---|
| IC Taq | AGTGGGACTCACCAACC (SEQ ID No. 4) | 17 |

A specific region for the TaqMan probe has been selected referring to Tm values calculated according to the nearest neighbor method.

"MYC Taq" is one TaqMan probe specifically annealing the pMYC plasmid, and "IC Taq" is another TaqMan probe specifically annealing the pICM5 plasmid. As fluorescent dye for both of "MYC Taq" and "IC Taq", "FAM" (registered trademark) has been used to be labeled at 5' end and "TAMRA" (registered trademark) has been used to be labeled at 3' end, respectively.

Production of the TaqMan probes has been performed by requesting custom synthesis to the Takara Bio Inc. Table 13 and Table 14 show composition of PCR solution and reaction conditions related thereto, respectively.

TABLE 13

Composition of PCR solution in TagMan Probe method

| Solution composition | Solution composition |
|---|---|
| MilliQ ™ water | — |
| PCR buffer | ×1 |
| dNTP Mix | 150 μM |
| MYC F | 0.50 μM |
| MYC R | 0.50 μM |
| MYC Taq | 0.30 μM |
| IC Taq | 0.30 μM |
| TakaRa Ex Taq ™ | 0.0125 U/μl |
| Target nucleic acid | — |

The above has been prepared to be 20 μL

TABLE 14

Reaction conditions in TaqMan probe method

| Reaction steps | Temperature (° C.) | | Time(s) |
|---|---|---|---|
| Initial denaturation | 95 | $T_0$ | 120 |
| Amplification | 95 | $T_0$ | 5 (FL measurement) |
| (1-44 cycles) | 70 | $T_1$ | 15 |
| | 72 | $T_2$ | 0 (FL measurement) |
| Second target NA detecting | 95 | $T_0$ | 5 (FL measurement) |
| | 50 | $T_3$ | 15 (FL measurement) |

The combination of 530 to 548 [nm] has been selected for excitation wavelength and fluorescent wavelength upon fluorescence measurement.

At a step for detecting the second target (95 Centigrade and 50 Centigrade) after amplification reaction, fluorescence measurement has been performed.

In Embodiment 4, fhyb.e has been defined as a fluorescence intensity value (50 Centigrade), and the same calculation except this point as Embodiment 1 has been conducted.

Determination in Embodiment 4 has been performed as below.

The F44 value of the measurement sample has been compared with Threshold 7. And, when the F44 value of the measurement sample is higher than Threshold 7, it has been determined that the first target nucleic acid is positive (existence), otherwise negative (nonexistence).

As Threshold 7, an average of F44 values of the negative reference plus three times the standard deviation (hereinafter, called as "mean+3SD") has been used.

Notwithstanding the first target nucleic acid is positive or negative, the Fs value has been compared with Threshold 8, and when the Fs value is higher than Threshold 8, it has been determined that the second target nucleic acid is positive (existence), otherwise negative (nonexistence).

As Threshold 8, the value of "mean+3SD" of a sample to which only the pMYC plasmid is added has been used.

A first Tm value of 75.8 Centigrade has been set for a sequence of MYC Taq, and a second Tm value of 53.7 Centigrade has been set for a sequence of IC Taq. For this reason, it has been estimated that probes anneal only MYC Taq during the temperature range (from 70 Centigrade to 95 Centigrade) in the PCR.

Since the fluorescence measurement with respect to the second target detection step has been carried out at 95 Centigrade and 50 Centigrade which is lower than the Tm value of IC Taq, it has been estimated that emission of both of MYC Taq and the IC Taq has been simultaneously detected according to measured values at the second target detection step.

Regarding an amplification curve of the negative reference, emission has not observed until 44 cycles when the PCR ends. This is because a value 1.028 of F44 is not higher than a value 1.028 of Threshold 7. At this time, "mean+3SD" is equal to 1.028 to be regarded as Threshold 7 for the first target detection, thereby being shown in Table 15. The amplification curve related thereto is also shown in FIG. 18.

Regarding another amplification curve of the pMYC plasmid of the first target nucleic acid, emission caused by annealing of MYC Taq has been observed from about 28 cycles. It has been revealed that a value 1.427 of F44 has been higher than Threshold 7, and further that the objective region of the pMYC plasmid has been amplified.

At this time, "mean+3SD" of Fs has been equal to 0.110 to be regarded as Threshold 8 for the second target detection, thereby being shown in Table 15. The amplification curve related thereto is also shown in FIG. 19.

TABLE 15

| | | Values used for determination in TaqMan Probe method | | |
| --- | --- | --- | --- | --- |
| | TE | pMYC | pICMS | pMYC pICM5 |
| F44 | 1.028 | 1.427 | 1.028 | 1.348 |
| F44 (Average + 3SD) | 1.028 ※1 | — | — | — |
| Fe | 1.060 | 1.536 | 1.158 | 1.525 |
| Fs | 0.032 | 0.109 | 0.130 | 0.177 |
| Fs (Average + 3SD) | | 0.110 ※2 | — | — |

※1 Threshold 7
※2 Threshold 8

Regarding an amplification curve of the pICM5 plasmid of the second target nucleic acid, no emission has been observed during the amplification reaction. This is because a value 1.028 of F44 is not higher than a value 1.028 of Threshold 7. A value 0.130 of Fs has been higher than Threshold 8.

The above-mentioned results have revealed that the objective region of the pMYC plasmid has been not amplified, further that the objective region of the pICM5 plasmid has been amplified.

Table 15 shows the value of the Fs. The amplification curve is shown in FIG. 20.

Regarding an amplification curve upon both the pMYC plasmid of the first target nucleic acid and the pICM5 plasmid of the second target nucleic acid have been added to the solution, emission caused by annealing of MYC EP has been observed from about 29 cycles as the same as the above-mentioned amplification curve of the pMYC plasmid. A value 1.348 of F40 has been higher than Threshold 7, and it has been revealed that the objective region of the pMYC plasmid has been amplified.

A value 0.177 of Fs is higher than Threshold 8, and it has been revealed that the objective region of the pICM5 plasmid has been amplified. Table 15 shows the value of the Fs. The amplification curve related thereto is shown in FIG. 21.

According to the above-mentioned results, it has been revealed that *Mycoplasma pneumoniae* P1 genes and internal control composition can be detected by means of one reaction vessel containing one kind of reaction solution and one kind of fluorescent labels when the method of designing probes and temperature profiles are incorporated with even the TaqMan probe method.

Embodiment 5

<Detection of *Mycoplasma pneumoniae* P1 Genes and Internal Control Composition Based on QProbe Method with Actual Specimen>

According to the QProbe method, *Mycoplasma pneumoniae* P1 genes and internal control composition have been detected by means of actual specimens.

As *Mycoplasma pneumoniae* P1 genes, first total DNA has been used, the first total DNA having been extracted from first pharynx wiping liquid of which *Mycoplasma pneumoniae* has been determined to be positive (tested by the BML, Inc.) according to the LAMP method (Japanese registered patent No. 3313358) by means of a "QIAamp" DNA mini Kit (registered trademark of the QIAGEN).

As negative samples, second total DNA has been used, the second total DNA having been extracted from second pharynx wiping liquid of which *Mycoplasma pneumoniae* has been determined to be negative according to the LAMP method by means of the "QIAamp" DNA mini Kit. PCR has been carried out under the same conditions other than this point as those of Embodiment 1.

The same calculation as Embodiment 1 has been performed on obtained raw data related thereto.

Determination in Embodiment 5 has been performed as below.

The F44 value of the measurement sample has been compared with Threshold 9. And, when the F44 value of the measurement sample is lower than Threshold 9, it has been determined that the first target nucleic acid is positive (existence), otherwise negative (nonexistence).

As Threshold 9, an average of F44 values of the negative reference minus three times the standard deviation (hereinafter, called as "mean−3SD") has been used.

Notwithstanding the first target nucleic acid is positive or negative, the Fs value has been compared with Threshold 10, and when the Fs value is lower than Threshold 10, it has been determined that the second target nucleic acid is positive (existence), otherwise negative (nonexistence). As Threshold 10, the value of "mean−3SD" with respect to Fs of the positive sample has been used.

Regarding an amplification curve of the negative reference, extinction has not observed until 44 cycles when the PCR ends. This is because a value 0.997 of F44 is not lower than a value 0.997 of Threshold 9. At this time, "mean−3SD" is equal to 0.997 to be regarded as Threshold 9 for the first target detection in this Embodiment, thereby being shown in Table 16. The amplification curve related thereto is also shown in FIG. 22.

Regarding another amplification curve of the positive reference of the first target nucleic acid, extinction caused by annealing of MYC QP has been observed from about 35 cycles. It has been revealed that a value 0.951 of F44 has been lower than Threshold 9, and further that the objective region of the pMYC plasmid has been amplified.

At this time, "mean–3SD" of Fs has been equal to –0.132 to be regarded as Threshold 10 for the second target detection, thereby being shown in Table 16. The amplification curve related thereto is also shown in FIG. 23.

Regarding an amplification curve of the pICM5 plasmid of the second target nucleic acid, no extinction has been observed during the amplification reaction. This is because a value 0.998 of F44 is not lower than a value 0.997 of Threshold 9. A value –0.227 of Fs has been lower than Threshold 10.

The above-mentioned results have revealed that the objective region of the pMYC plasmid has been not amplified, further that the objective region of the pICM5 plasmid has been amplified. A value of Fs is shown in Table 16, and the amplification curve related thereto is also shown in FIG. 24.

Regarding an amplification curve upon the positive reference of the first target nucleic acid has been added to the pICM5 plasmid of the second target nucleic acid, extinction caused by annealing of MYC QP has been observed from about 35 cycles as the same as the amplification curve of the positive reference. A value 0.953 of F44 has been lower than Threshold 9, and it has been revealed that the objective region of the pMYC plasmid has been amplified.

A value –0.235 of Fs is lower than Threshold 10, and it has been revealed that the objective region of the pICM5 plasmid has been amplified. Table 16 shows the value of the Fs. The amplification curve related thereto is shown in FIG. 25.

TABLE 16

Values used for determination in QProbe method with actual specimen

| | negative sample | | positive sample | | pICMS | positive sample pICM5 |
|---|---|---|---|---|---|---|
| F44 | 0.997 | | 0.951 | | 0.998 | 0.953 |
| F44 (Average – 3SD) | 0.997 | ※1 | — | | — | — |
| Fe | 0.920 | | 0.824 | | 0.771 | 0.718 |
| Fs | –0.077 | | –0.127 | | –0.227 | –0.235 |
| Fs (Average – 3SD) | — | | –0.132 | ※2 | — | — |

※1 Threshold 9
※2 Threshold 10

According to the above-mentioned results, it has been revealed that *Mycoplasma pneumoniae* P1 genes and internal control composition can be detected by means of one reaction vessel containing one kind of reaction solution and one kind of fluorescent labels when the method of designing probes and temperature profiles are incorporated with the actual clinical specimens.

The present invention is also applicable for identifying subtypes and/or single nucleotide polymorphism of pathogenic organisms causing infectious diseases.

Embodiment 6

<Detection of *Chlamydia trachomatis* Endogeneous Plasmid Gene and *Neisseria gonorrhoeae* CMT Gene Based on QProbe Method>

According to the QProbe method, detection of *Chlamydia trachomatis* endogeneous plasmid genes and *Neisseria gonorrhoeae* CMT genes has been carried out.

(pCT)

Production of pCT plasmids has been performed by requesting custom synthesis to the Hokkaido System Science Co., Ltd. Gene fragments of common endogenous plasmids (pLGV440) of *Chlamydia trachomatis* which are pathogenic organisms causing *Chlamydia* infection have been artificially synthesized into plasmid DNA to be incorporated into a pUC57 vector, thereby having prepared the pCT plasmids.

(pNG)

Production of pNG plasmids has also been performed by requesting custom synthesis to the Hokkaido System Science Co., Ltd. Gene fragments of cytosine DNA methyl transferase (CMT) of *Neisseria gonorrhoeae* which is a pathogenic organism causing gonorrhea have been artificially synthesized into plasmid DNA to be incorporated into a pUC57 vector, thereby having prepared the pNG plasmids.

First length of the pCT plasmid is 3064 [bp], and second length of the pNG plasmid is 3059 [bp].

Based on the first and second length and the concentration ($\mu g/\mu l$) of plasmid solution, the number of copies per 1 [$\mu l$] has been calculated. After that, by means of TE buffer solution (10 [mM] Tris-HCl, 1.0 [mM] EDTA pH: 8.0), both of the pCT plasmids and the pNG plasmids have been diluted to be $1\times10^5$ [copies/pd].

Primer pairs used in the PCR method in Embodiment 6 are as shown in Table 17.

TABLE 17

Primers used for PCR in this Embodiment

| Probe name | Sequence (5'→3') | Length (bp) |
|---|---|---|
| CT F | TGAGCACCCTAGGCGTTTGTACTCCGTCAC (SEQ ID No. 6) | 30 |
| CT R | GCACTTTCTACAAGAGTACATCGGTCAACGAAGAGG (SEQ ID No. 7) | 36 |
| NG F | GGGCGTGGTTGAACTGGCAAAAAGC (SEQ ID No. 8) | 25 |
| NG R | CAGTGATTTTGGCATTGGCGATATTGG (SEQ ID No. 9) | 27 |

Information of thEprobes used in the PCR method in Embodiment 6 is as shown in Table 18.

TABLE 18

Probes used for PCR in this Embodiment

| Probe name | Sequence (5'→3') | Length (bp) |
|---|---|---|
| CT QP | TGCGGGCGATTTGCCTTAACCCCACC (SEQ ID No. 10) | 26 |
| NG QP | CTAAGCAAAATTCGAGGGGGAAAAC (SEQ ID No. 11) | 25 |

Based on a basic sequence of PCR products capable of being amplified by means of the pair of primers of SEQ ID NO: 6 and SEQ ID NO: 7, a specific region for CT QP has been selected referring to Tm values calculated with a QProbe design support tool on the J-Bio21 Center home pages.

Based on a basic sequence of PCR products capable of being amplified by means of the pair of primers of SEQ ID NO: 8 and SEQ ID NO; 9, a specific region for NG QP has been selected referring to Tm values calculated with the QProbe design support tool on the J-Bio21 Center home pages.

"CT QP" is one QProbe specifically annealing the pCT plasmid, and "NG QP" is another QProbe specifically annealing the pNG plasmid. As fluorescent dye for both of "CT QP" and "NG QP", "BODIPY FL" (registered trademark) has been used to label "C" at Y ends, respectively.

Production of the QProbes has been performed by requesting custom synthesis to the NIPPON STEEL & SUMIKIN Eco-Tech Corporation. Table 19 and Table 20 show composition of PCR solution and reaction conditions related thereto, respectively.

TABLE 19

| Composition of PCR solution | |
| --- | --- |
| Solution composition | Final concentration |
| MilliQ ™ water | — |
| PCR buffer | ×1 |
| dNTP Mix | 150 µM |
| CT F | 0.200 µM |
| CT R | 0.60 µM |
| CT QP | 0.15 µM |
| NG F | 0.20 µM |
| NG R | 0.60 µM |
| NG QP | 0.15 µM |
| KOD exo (—) DNA Polymerase | 0.0125 U/µl |
| Target nucleic acid | — |

The above has been prepared to be 20 µL

TABLE 20

| Reaction conditions of CT NG in QProbe method | | | |
| --- | --- | --- | --- |
| Reaction steps | Temperature (° C.) | | Time(s) |
| Initial denaturation | 95 | $T_0$ | 120 |
| Amplification | 95 | $T_0$ | 5 (FL measurement) |
| (1-44 cycles) | 68 | $T_1, T_2$ | 15 (FL measurement) |
| Second target NA detecting | 95 | $T_0$ | 5 (FL measurement) |
| | 55 | $T_3$ | 15 (FL measurement) |

The combination of 510 to 528 [nm] has been selected for excitation wavelength and fluorescent wavelength upon fluorescence measurement.

Fluorescence values have been measured at the denaturation step (95 Centigrade) and the elongation step (68 Centigrade) for every cycle. Furthermore, after the amplification reaction has been completed, at a step for detecting the second target (95 Centigrade and 55 Centigrade), fluorescence measurement has been performed.

The same calculation as that of Embodiment 1 has been performed on obtained raw data related thereto.

Determination according to the QProbe method has been performed using the method shown below.

The F44 value of the measurement sample has been compared with Threshold 11. And, when the F44 value of the measurement sample is lower than Threshold 11, it has been determined that the first target nucleic acid is positive (existence), otherwise negative (nonexistence).

As Threshold 11, an average of F44 values of the negative reference minus three times the standard deviation (hereinafter, called as "mean–3SD") has been used.

Notwithstanding the first target nucleic acid is positive or negative, the Fs value has been compared with Threshold 12, and when the Fs value is lower than Threshold 12, it has been determined that the second target nucleic acid is positive (existence), otherwise negative (nonexistence).

As Threshold 12, the value of "mean–3SD" of a sample to which only the pNG plasmid is added has been used.

A first Tm value of 73.4 Centigrade has been set for a sequence of CT QP, and a second Tm value of 62.5 Centigrade has been set for a sequence of NG QP. For this reason, it has been estimated that probes anneal only CT QP during the temperature range (from 68 Centigrade to 95 Centigrade) in the PCR.

Since the fluorescence measurement with respect to the second target detection step has been carried out at 95 Centigrade and 55 Centigrade which is lower than the Tm value of NG QP, it has been estimated that extinction of both of CT QP and the NG QP has been simultaneously detected according to measured values at the second target detection step.

Regarding an amplification curve of the negative reference, extinction has not observed until 44 cycles when the PCR ends. This is because a value 0.998 of F44 is not lower than a value 0.996 of Threshold 11. At this time, "mean–3SD" is equal to 0.996 to be regarded as Threshold 11 for the first target detection in this Embodiment, thereby being shown in Table 21. The amplification curve related thereto is also shown in FIG. 26.

Regarding another amplification curve of the pCT plasmid of the first target nucleic acid, extinction caused by annealing of CT QP has been observed from about 28 cycles. It has been revealed that a value 0.720 of F44 has been lower than Threshold 11, and further that the objective region of the pCT plasmid has been amplified.

At this time, "mean–3SD" of Fs has been equal to –0.039 to be regarded as Threshold 12 for the second target detection, thereby being shown in Table 21. The amplification curve related thereto is also shown in FIG. 27.

Regarding an amplification curve of the pNG plasmid of the second target nucleic acid, no extinction has been observed during the amplification reaction. This is because a value 0.998 of F44 is not lower than a value 0.9% of Threshold 11. A value –0.065 of Fs has been lower than Threshold 12.

The above-mentioned results have revealed that the objective region of the pCT plasmid has been not amplified, further that the objective region of the pNG plasmid has been amplified. Table 21 shows the value of the Fs. The amplification curve is shown in FIG. 28.

TABLE 21

| Values used for determination of second item in QProbe method | | | | |
| --- | --- | --- | --- | --- |
| | TE | pCT | pNG | pCT pNG |
| F44 | 0.998 | 0.720 | 0.998 | 0.729 |
| F44 (Average – 3SD) | 0.996 ·✕·1 | — | — | — |
| Fe | 1.009 | 0.681 | 0.933 | 0.618 |
| F5 | 0.011 | ——0.039 | –0.065 | –0.111 |
| Fs (Average – 3SD) | — | –0.039·✕·2 | — | — |

✕·1 Threshold 11
✕·2 Threshold 12

Regarding an amplification curve upon both the pCT plasmid of the first target nucleic acid and the pNG plasmid of the second target nucleic acid have been added to the solution, extinction caused by annealing of CT QP has been observed from about 28 cycles as the same as the above-mentioned amplification curve of the pCT plasmid. A value 0.729 of F44 has been lower than Threshold 11, and it has been revealed that the objective region of the pCT plasmid has been amplified.

A value −0.111 of Fs is lower than Threshold 12, and it has been revealed that the objective region of the pNG plasmid has been amplified. Table 21 shows the value of the Fs. The amplification curve related thereto is shown in FIG. 29.

According to the above-mentioned results, it has been revealed that *Mycoplasma pneumoniae* P1 genes and internal control composition can be detected by means of one reaction vessel containing one kind of reaction solution and one kind of fluorescent labels when the method of designing probes and temperature profiles are incorporated with two items of genes.

Embodiment 7

<Detection of *Mycoplasma pneumoniae* P1 Genes and Internal Control Composition Based on QProbe Method to Detect Plural Times the Second Target in Amplification Reaction>

Not only after the final cycle but also during the amplification reaction, the second target detection step has been carried out in an inserted manner, and detection of *Mycoplasma pneumoniae* P1 genes and internal control composition has been performed based on the QProbe method.

The primers, probes, reaction solution composition, and nucleic acids have been used for the PCR method as the same as Embodiment 1. Table 22 shows reaction conditions thereof.

TABLE 22

Reaction conditions of second target detecting step in QProbe method in Embodiment 7

| Reaction steps | Temperature (° C.) | | Time(s) |
|---|---|---|---|
| Initial denaturation | 95 | $T_0$ | 120 |
| Amplification (1-20 cycles) | 95 | $T_0$ | 10 (FL measurement) |
| | 70 | $T_1$ | 10 |
| | 72 | $T_2$ | 10 (FL measurement) |
| Second target NA detecting first time | 95 | $T_0$ | 10 (FL measurement) |
| | 55 | $T_3$ | 10 (FL measurement) |
| Amplification (21-27 cycles) | 95 | $T_0$ | 10 (FL measurement) |
| | 70 | $T_1$ | 10 |
| | 72 | $T_2$ | 10 (FL measurement) |
| Second target NA detecting second time | 95 | $T_0$ | 10 (FL measurement) |
| | 55 | $T_3$ | 10 (FL measurement) |
| Amplification (28-34 cycles) | 95 | $T_0$ | 10 (FL measurement) |
| | 70 | $T_1$ | 10 |
| | 72 | $T_2$ | 10 (FL measurement) |
| Second target NA detecting third time | 95 | $T_0$ | 10 (PL measurement) |
| | 55 | $T_3$ | 10 (FL measurement) |
| Amplification (35-41 cycles) | 95 | $T_0$ | 10 (FL measurement) |
| | 70 | $T_1$ | 10 |
| | 72 | $T_2$ | 10 (FL measurement) |
| Second target NA detecting fourth time | 95 | $T_0$ | 10 (FL measurement) |
| | 55 | $T_3$ | 10 (FL measurement) |

FIG. 30 is a graph of changes of temperature in the amplification reaction.

In analysis of Embodiment 7, the same steps as Embodiment 1 except the following calculation have been carried out.

$$fen = fhyb.en/fden.en \qquad \text{(Formula 4)}$$

herein.

fen: fluorescence intensity value in n times second target detection step calculated according to Formula 4;

fhyb.en: fluorescence intensity value (55 Centigrade) in n times second target detection step; and fden.en: fluorescence intensity value (95 Centigrade) in n times second target detection step.

$$Fen = fen/f10 \qquad \text{(Formula 5)}$$

herein,

Fen: relative value in n times second target detection step assuming that the fluorescence intensity value in the tenth cycle obtained according to Formula 4 is equal to a value of "1."

$$Fs1 = Fe1 - F20 \qquad \text{(Formula 6)}$$

$$Fs2 = Fe2 - F27 \qquad \text{(Formula 6')}$$

$$Fs3 = Fe3 - F34 \qquad \text{(Formula 6'')}$$

$$Fs4 = Fe4 - F41 \qquad \text{(Formula 6''')}$$

herein,

Fs1: measurement value in first time second target detection step;

Fs2: measurement value in second time second target detection step;

Fs3: measurement value in third time second target detection step; and

Fs4: measurement value in fourth time second target detection step.

Determination has been performed using the method shown below.

The F41 value of the measurement sample has been compared with Threshold 13. And, when the F41 value of the measurement sample is lower than Threshold 13, it has been determined that the first target nucleic acid is positive (existence), otherwise negative (nonexistence).

As Threshold 13, an average of F41 values of the negative reference minus three times the standard deviation (hereinafter, called as "mean–3SD") has been used.

In the first time second target detection step, the Fs1 value has been compared with Threshold 14, and when the Fs1 value is lower than Threshold 14, it has been determined that the second target nucleic acid is positive (existence), otherwise negative (nonexistence).

As Threshold 14, the value of "mean–3SD" regarding the Fs1 value of a sample to which only the pMYC plasmid is added has been used.

In the second time second target detection step, the Fs2 value has been compared with Threshold 15, and when the Fs2 value is lower than Threshold 15 it has been determined that the second target nucleic acid is positive (existence), otherwise negative (nonexistence).

As Threshold 15, the value of "mean–3SD" regarding the Fs2 value of a sample to which only the pMYC plasmid is added has been used.

In the third time second target detection step, the Fs3 value has been compared with Threshold 16, and when the first target detection in this Embodiment, thereby being shown in Table 23. The amplification curve related thereto is also shown in FIG. 31.

Regarding another amplification curve of the pMYC plasmid of the first target nucleic acid, extinction caused by annealing of MYC QP has been observed from about 30 cycles. It has been revealed that a value 0.892 of F41 has been lower than Threshold 13, and further that the objective region of the pMYC plasmid has been amplified.

At this time, "mean–3SD" of Fs1 has been equal to –0.058, "mean–3SD" of Fs2 has been equal to –0.070, "mean–3SD" of Fs3 has been equal to –0.080, and "mean–3SD" of Fs4 has been equal to –0.087 to be regarded as Threshold 14, Threshold 15, Threshold 16, and Threshold 17 for the second target detection, respectively, thereby being shown in Table 23. The amplification curve related thereto is also shown in FIG. 32.

TABLE 23

| | | | | |
|---|---|---|---|---|
| Values used for determination at second target detecting step in QProbe method in Embodiment 7 | | | | |
| | TE | pMYC | pICM5 | pMYC pICM5 |
| F20 | 0.999 | 0.999 | 0.999 | 0.999 |
| Fe1 | 0.941 | 0.941 | 0.941 | 0.941 |
| Fs1 | –0.058 | –0.058 | –0.058 | –0.058 |
| Fs1 (Average – 3SD) | — | –0.058 ✕2 | — | — |
| F27 | 0.999 | 0.999 | 1.000 | 0.999 |
| Fe2 | 0.941 | 0.930 | 0.943 | 0.930 |
| Fs2 | –0.058 | –0.068 | –0.057 | –0.068 |
| Fs2 (Average – 3SD) | — | –0.070 ✕3 | — | — |
| F34 | 0.999 | 0.949 | 1.000 | 0.951 |
| Fe3 | 0.941 | 0.870 | 0.916 | 0.842 |
| Fs3 | –0.058 | –0.079 | –0.084 | –0.109 |
| Fs3 (Average – 3SD) | — | –0.080 ✕4 | — | — |
| F41 | 0.999 | 0.892 | 0.999 | 0.897 |
| F41 (Average – 3SD) | 0.998 ✕1 | — | — | — |
| Fe4 | 0.940 | 0.812 | 0.805 | 0.743 |
| Fs4 | –0.058 | –0.080 | –0.192 | –0.154 |
| Fs4 (Average – 3SD) | — | –0.087 ✕5 | — | — |

✕1 Threshold 13
✕2 Threshold 14
✕3 Threshold 15
✕4 Threshold 16
✕5 Threshold 17

Fs3 value is lower than Threshold 16 it has been determined that the second target nucleic acid is positive (existence), otherwise negative (nonexistence).

As Threshold 16, the value of "mean–3SD" regarding the Fs3 value of a sample to which only the pMYC plasmid is added has been used.

In the fourth time second target detection step, the Fs4 value has been compared with Threshold 17, and when the Fs4 value is lower than Threshold 17 it has been determined that the second target nucleic acid is positive (existence), otherwise negative (nonexistence).

As Threshold 17, the value of "mean–3SD" regarding the Fs4 value of a sample to which only the pMYC plasmid is added has been used.

Regarding an amplification curve of the negative reference, extinction has not been observed until 41 cycles when the PCR ends. This is because a value 0.999 of F41 is not lower than a value 0.998 of Threshold 13. At this time, "mean–3SD" is equal to 0.998 to be regarded as Threshold 13 for the Regarding an amplification curve of the pICM5 plasmid of the second target nucleic acid, no extinction has been observed during the amplification reaction except in the respective second target detection steps. This is because a value 0.999 of F41 is not lower than a value 0.998 of Threshold 13. A value –0.058 of Fs1 has been higher than Threshold 14, and it has been revealed that the objective region of the pICM5 plasmid has not been amplified up to an identification limit until the first time second target detection step.

A value –0.057 of Fs2 has been higher than Threshold 15, and it has been revealed that the objective region of the pICM5 plasmid has not been amplified up to the identification limit until the second time second target detection step.

A value –0.084 of Fs3 has been lower than Threshold 16, and it has been revealed that the objective region of the pICM5 plasmid has been amplified beyond the identification limit until the third time second target detection step.

A value −0.192 of Fs4 has also been lower than Threshold 17. Table 23 shows the values of the Fs1, Fs2, Fs3 and Fs4. The amplification curves are shown in FIG. 33.

Regarding an amplification curve upon both the pMYC plasmid of the first target nucleic acid and the pICM5 plasmid of the second target nucleic acid have been added to the solution, extinction caused by annealing of MYC QP has been observed from about 30 cycles as the same as the amplification curve of the pMYC plasmid. A value 0.897 of F41 has been lower than Threshold 13, and it has been revealed that the objective region of the pMYC plasmid has been amplified.

A value −0.058 of Fs1 has been higher than Threshold 14, and it has been revealed that the objective region of the pICM5 plasmid has not been amplified beyond the identification limit until the first time second target detection step.

A value −0.068 of Fs2 has been also higher than Threshold 15, and it has been revealed that the objective region of the pICM5 plasmid has not been amplified beyond the identification limit until the second time second target detection step.

A value −0.109 of Fs3 has been lower than Threshold 16, and it has been revealed that the objective region of the pICM5 plasmid has been amplified beyond the identification limit until the third time second target detection step.

A value −0.154 of Fs4 has also been lower than Threshold 17. Table 23 shows the values of the Fs1, Fs2, Fs3 and Fs4. The amplification curves are shown in FIG. 34.

According to the above-mentioned results, also in a case where the second target detection step has been carried out in the inserted manner not only after the final cycle but also within the amplification reaction, it has been revealed that *Mycoplasma pneumoniae* P1 genes and internal control composition can be detected.

BRIEF DESCRIPTION OF THE DRAWINGS

FIG. 37(*b*) is an explanatory diagram of an annealing step in Embodiment 1 according to the present invention;

FIG. 37(*c*) is an explanatory diagram of an elongation step in Embodiment 1 according to the present invention;

FIG. 37(*d*) is an explanatory diagram of an elongation-completed step in Embodiment 1 according to the present invention:

FIG. 38(*b*) is an explanatory diagram of the annealing step in Embodiment 1 according to the present invention.

BRIEF DESCRIPTION OF SYMBOLS

Figure 1:
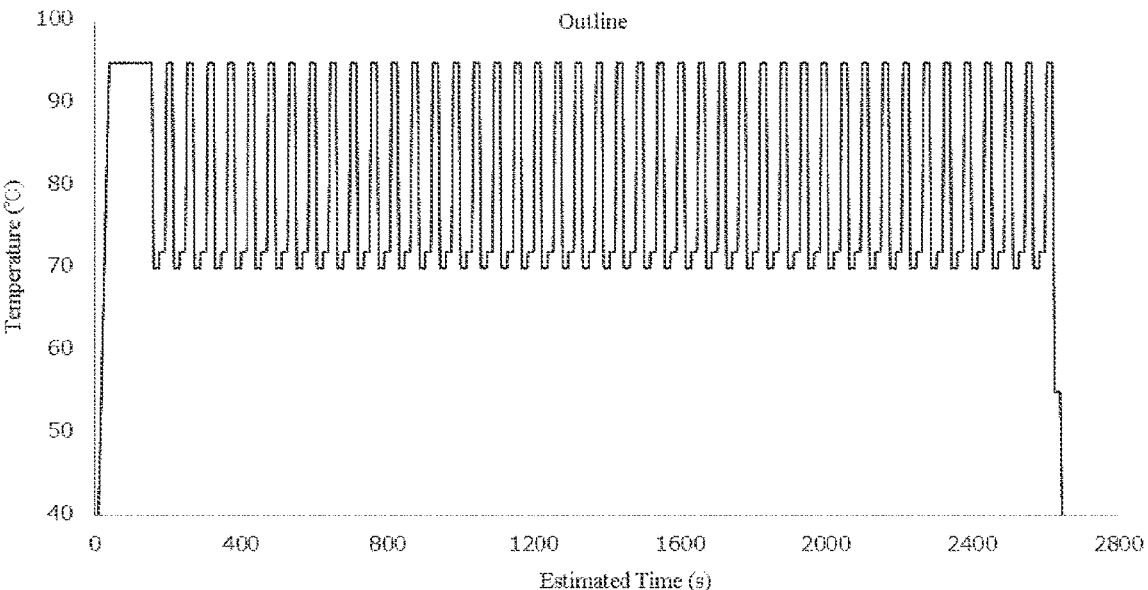
FIG. 1 is a graph showing changes of temperature within mixed-solution in Embodiment 1 according to the present invention.
Figure 2:
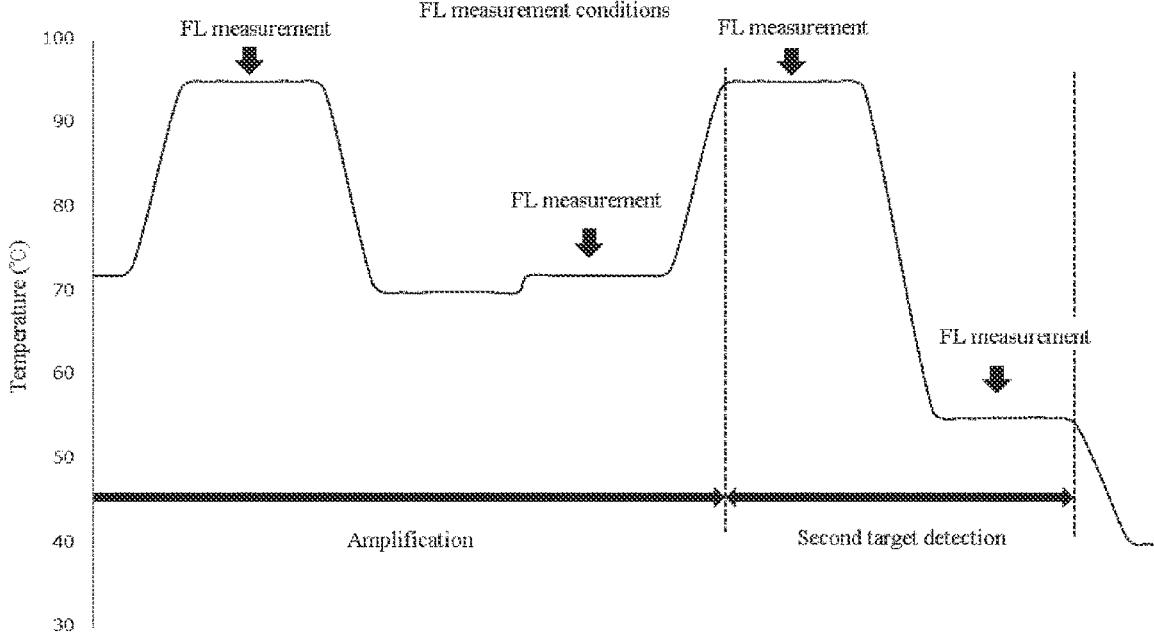
FIG. 2 is a timing explanatory diagram of fluorometry in Embodiment 1 according to the present invention.
Figure 3:
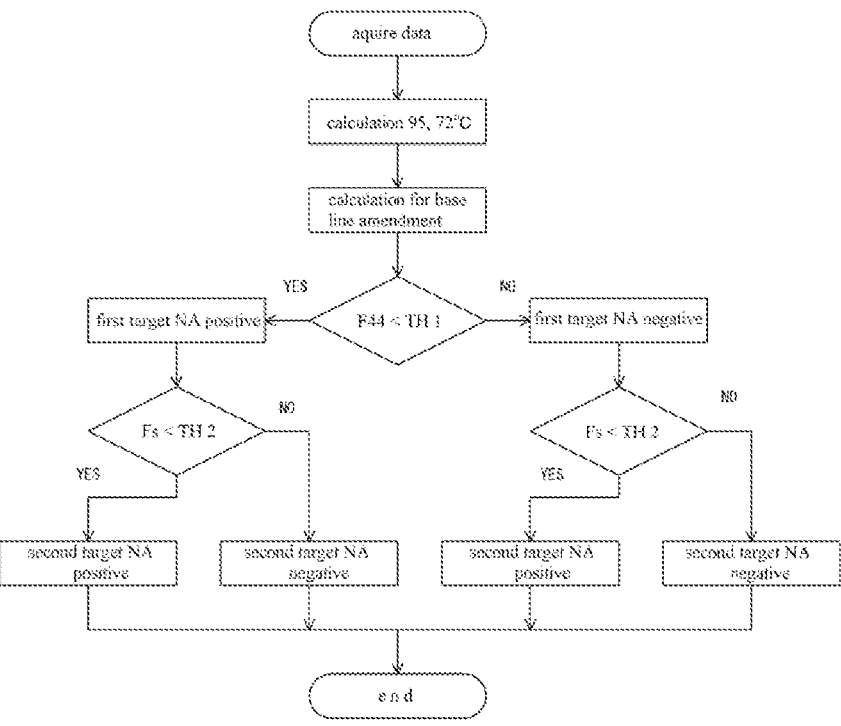
FIG. 3 is a flow chart showing a determination method in Embodiment 1 according to the present invention.
Figure 4:
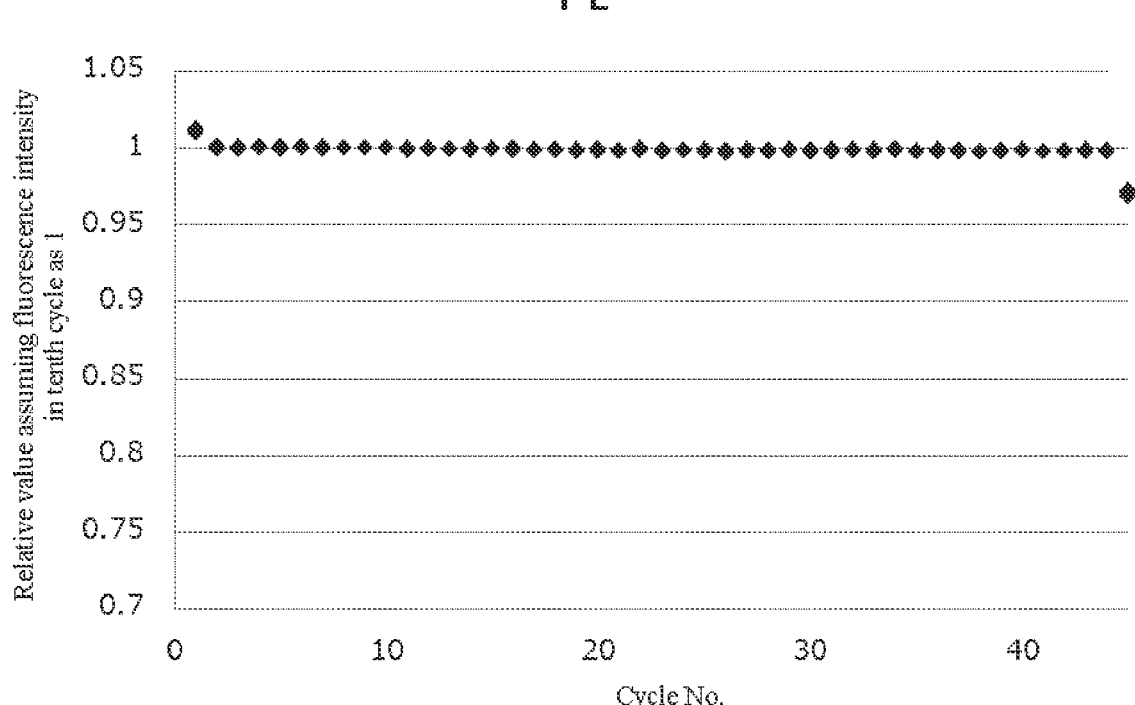
FIG. 4 is a graph showing changes of fluorescence intensity regarding a negative reference in Embodiment 1 according to the present invention.
Figure 5:
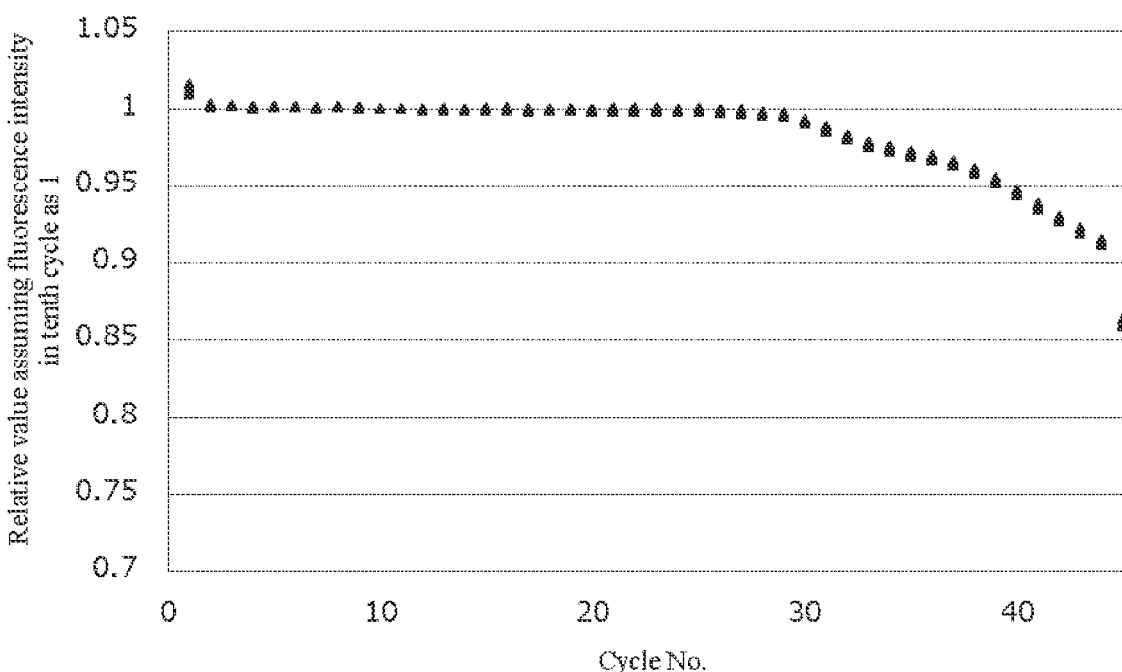
FIG. 5 is a graph showing changes of fluorescence intensity regarding a first target nucleic acid in Embodiment 1 according to the present invention.
Figure 6:
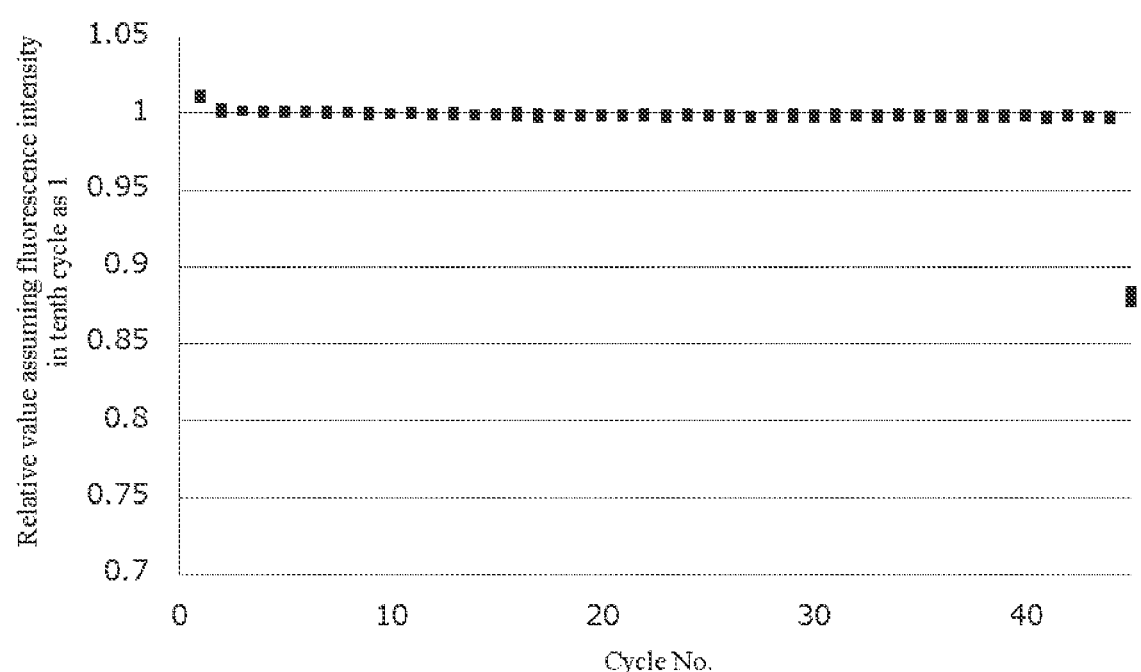
FIG. 6 is a graph showing changes of fluorescence intensity regarding a second target nucleic acid in Embodiment 1 according to the present invention.
Figure 7:
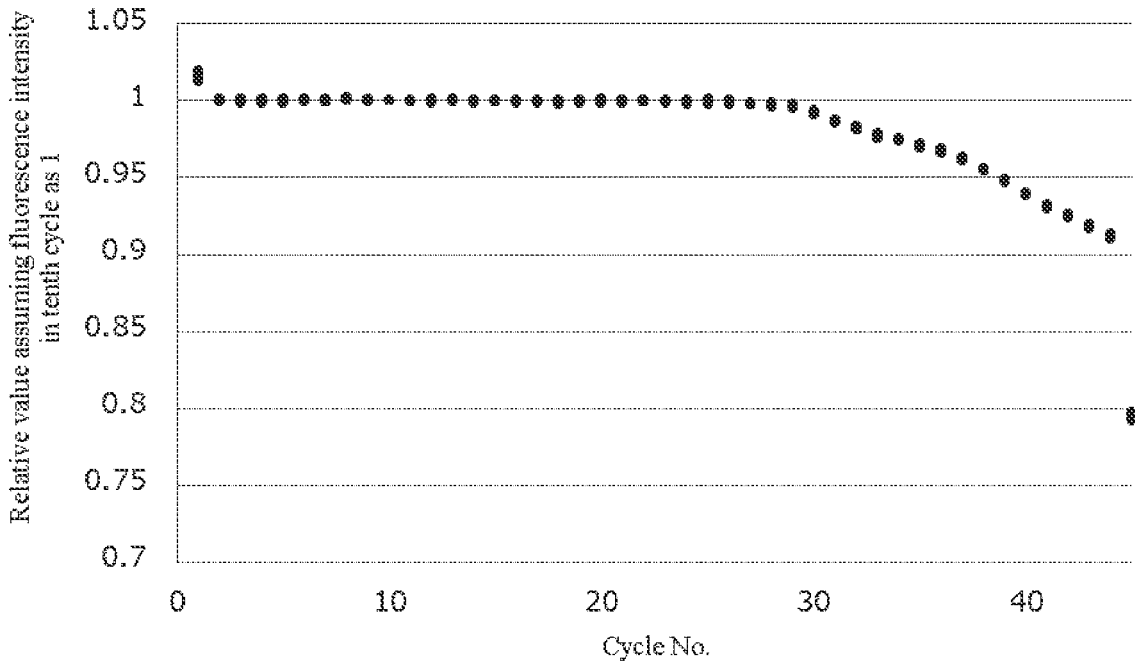
FIG. 7 is a graph showing changes of fluorescence intensity regarding the first target nucleic acid and the second target nucleic acid in Embodiment 1 according to the present invention.
Figure 8:
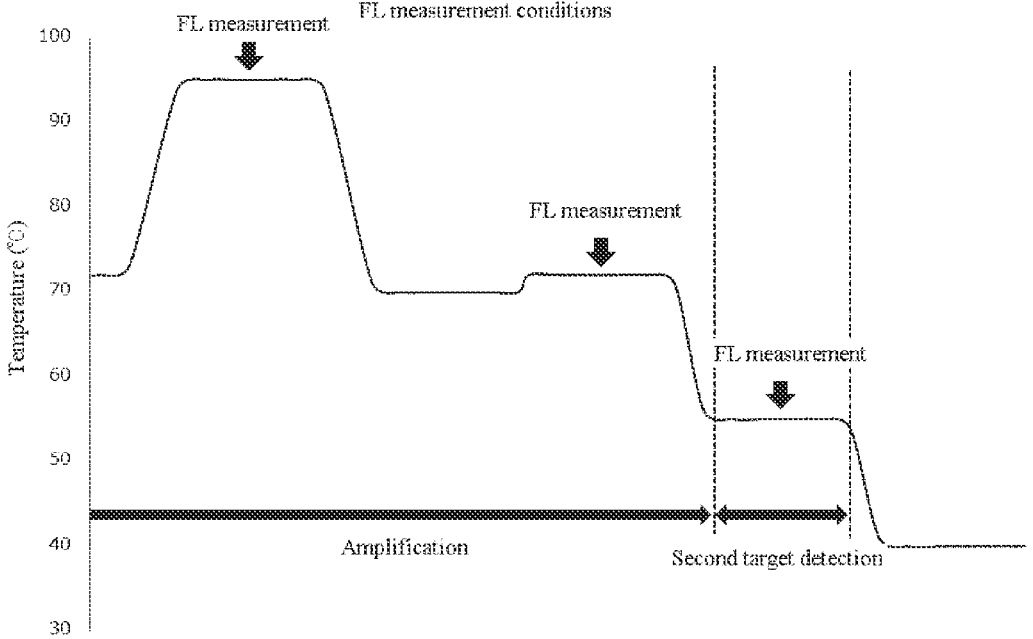
FIG. 8 is a timing explanatory diagram of fluorometry in Embodiment 2 according to the present invention.
Figure 9:
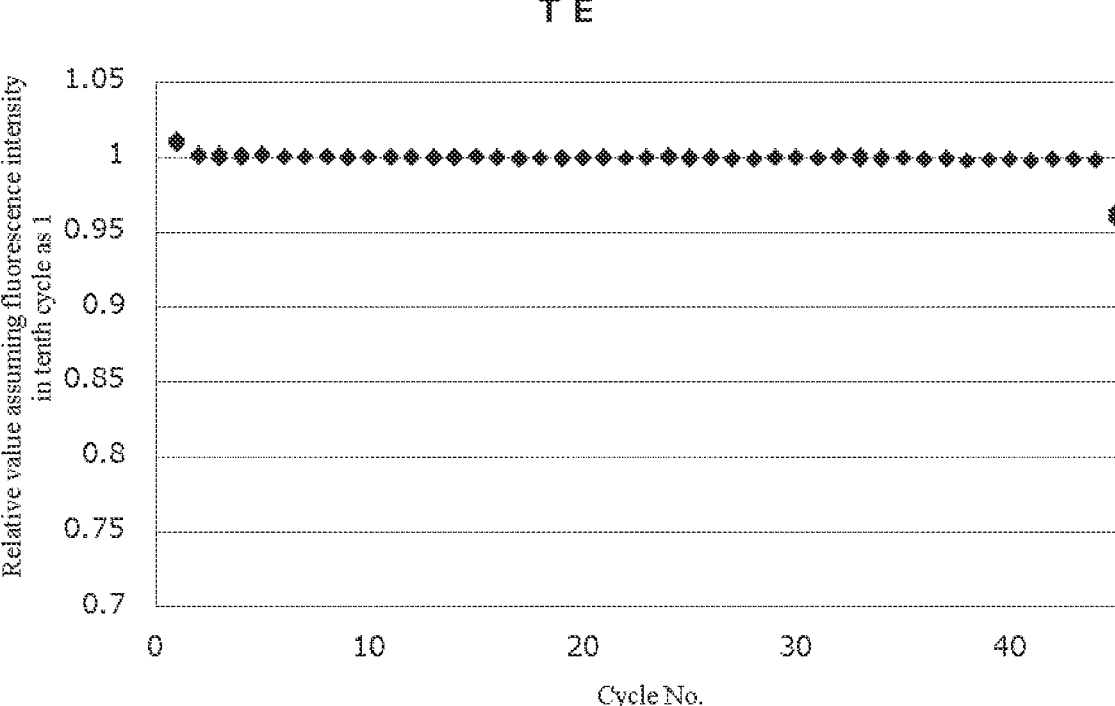
FIG. 9 is a graph showing changes of fluorescence intensity regarding a negative reference in Embodiment 2 according to the present invention.
Figure 10:
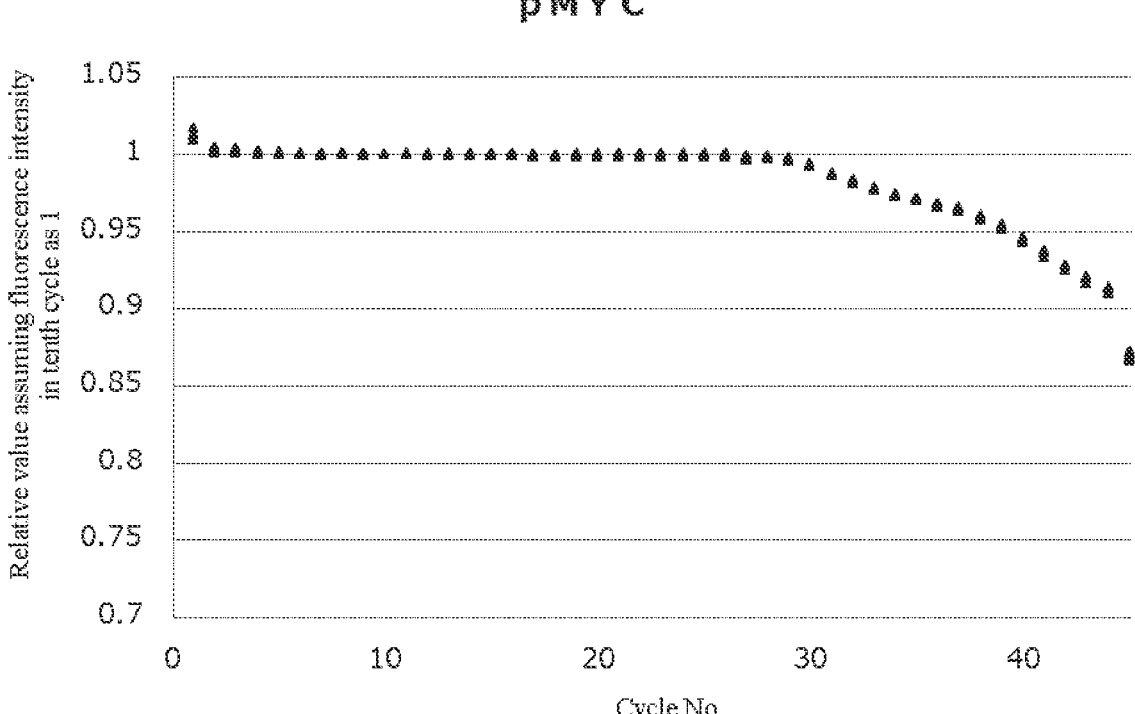
FIG. 10 is a graph showing changes of fluorescence intensity regarding a first target nucleic acid in Embodiment 2 according to the present invention.
Figure 11:
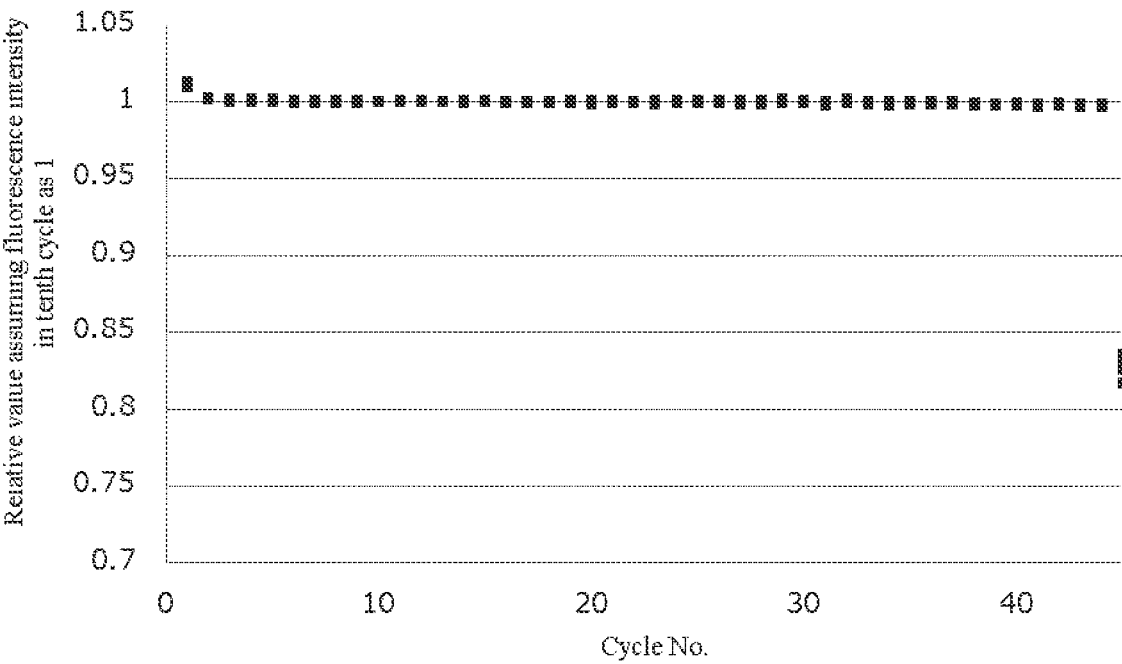
FIG. 11 is a graph showing changes fluorescence intensity regarding a second target nucleic acid in Embodiment 2 according to the present invention.
Figure 12:
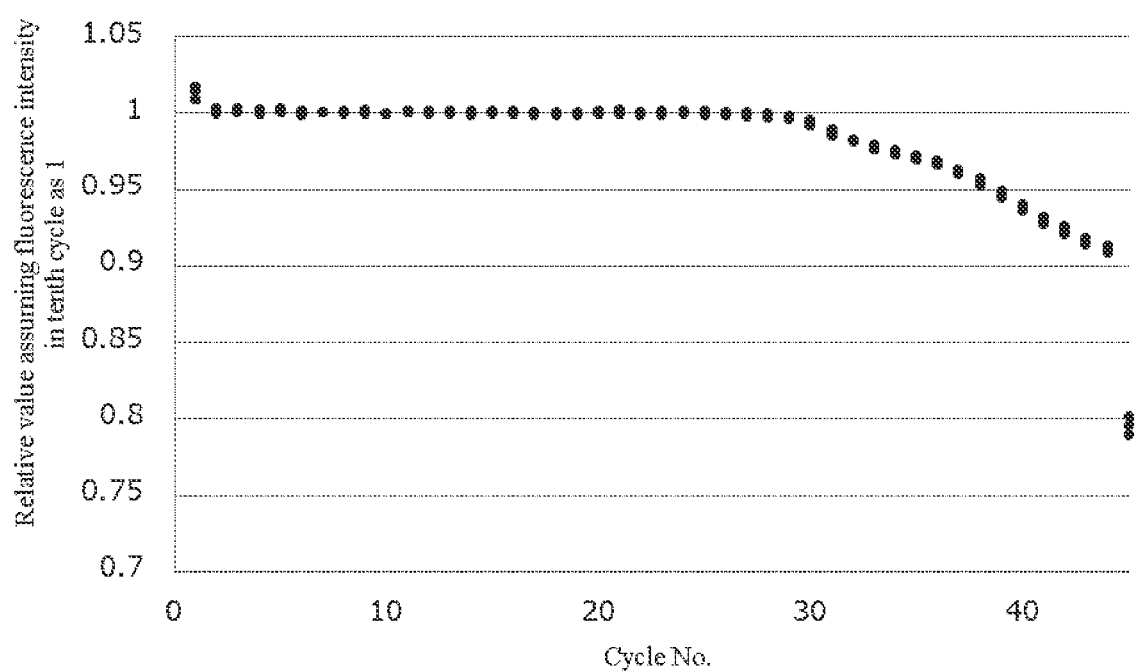
FIG. 12 is a graph showing changes of fluorescence intensity regarding the first target nucleic acid and the second target nucleic acid in Embodiment 2 according to the present invention.
Figure 13:
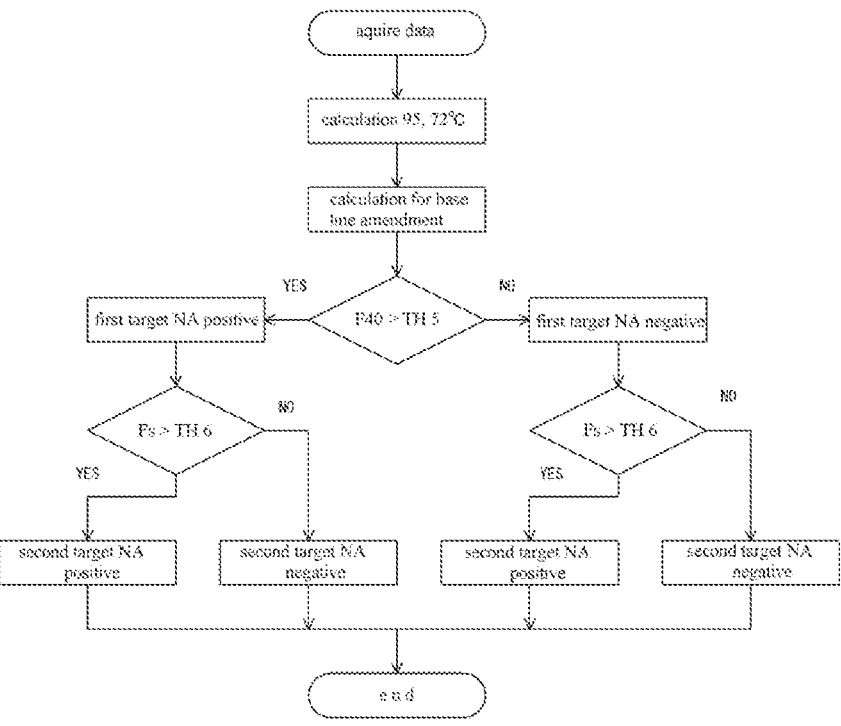
FIG. 13 is a flow chart showing a determination method in Embodiment 3 according to the present invention.
Figure 14:
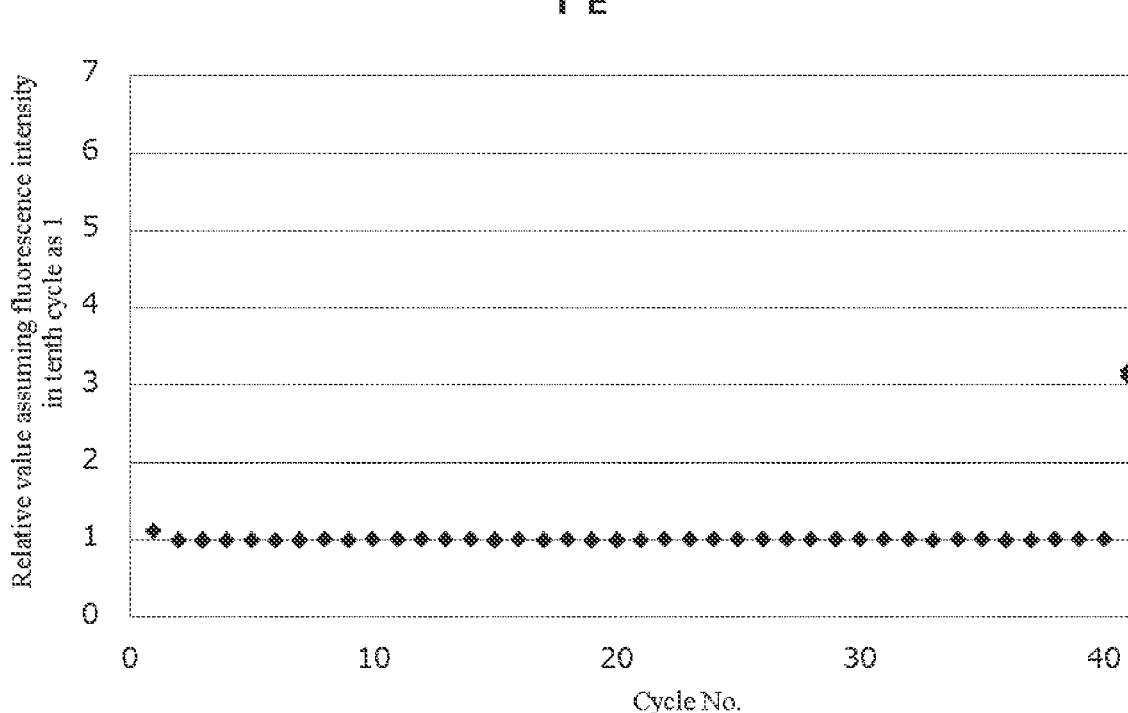
FIG. 14 is a graph showing changes of fluorescence intensity regarding a negative reference in Embodiment 3 according to the present invention.
Figure 15:
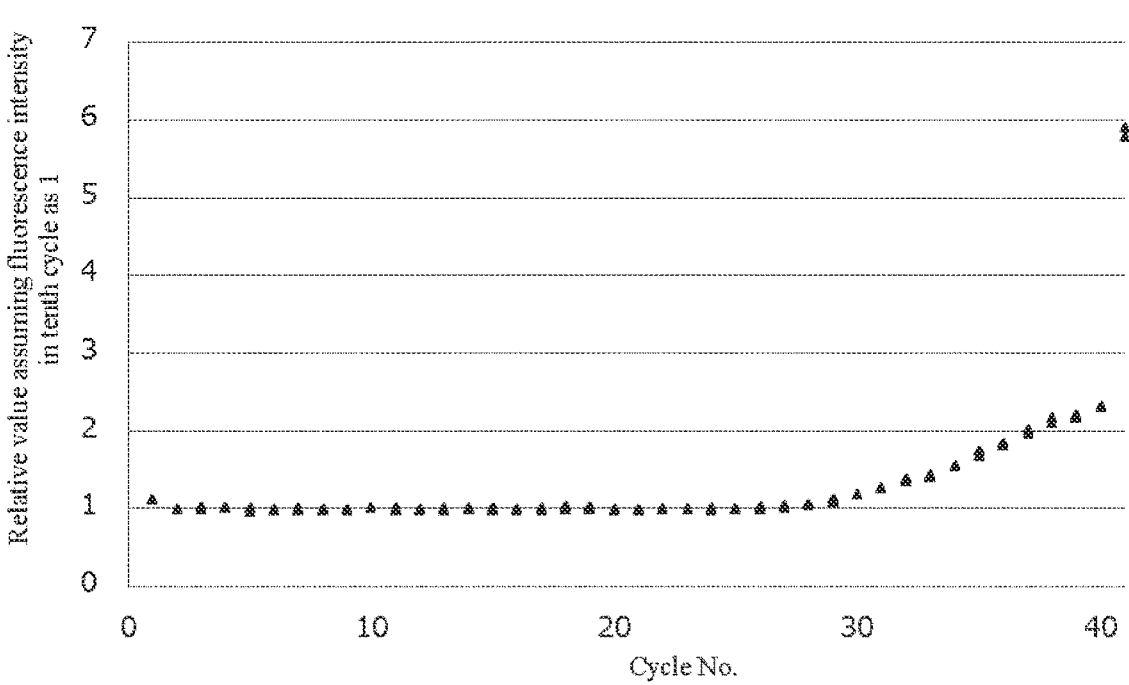
FIG. 15 is a graph showing changes of fluorescence intensity regarding a first target nucleic acid in Embodiment 3 according to the present invention.
Figure 16:
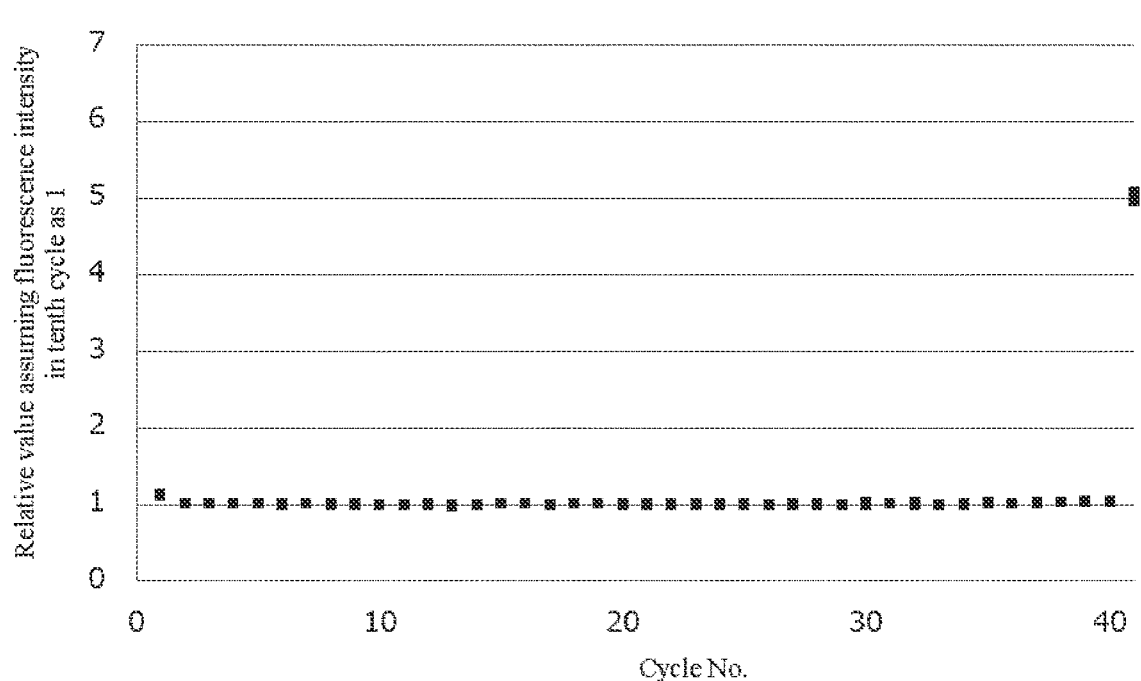
FIG. 16 is a graph showing changes of fluorescence intensity regarding a second target nucleic acid in Embodiment 3 according to the present invention.
Figure 17:
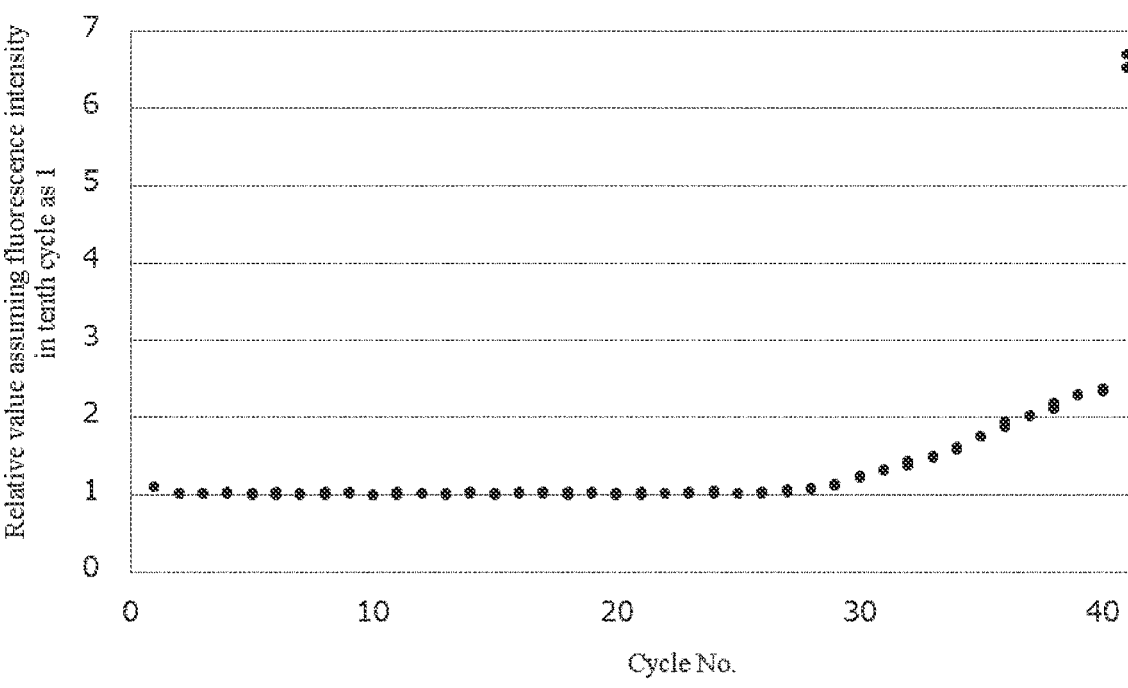
FIG. 17 is a graph showing changes of fluorescence intensity regarding the first target nucleic acid and the second target nucleic acid in Embodiment 3 according to the present invention.
Figure 18:
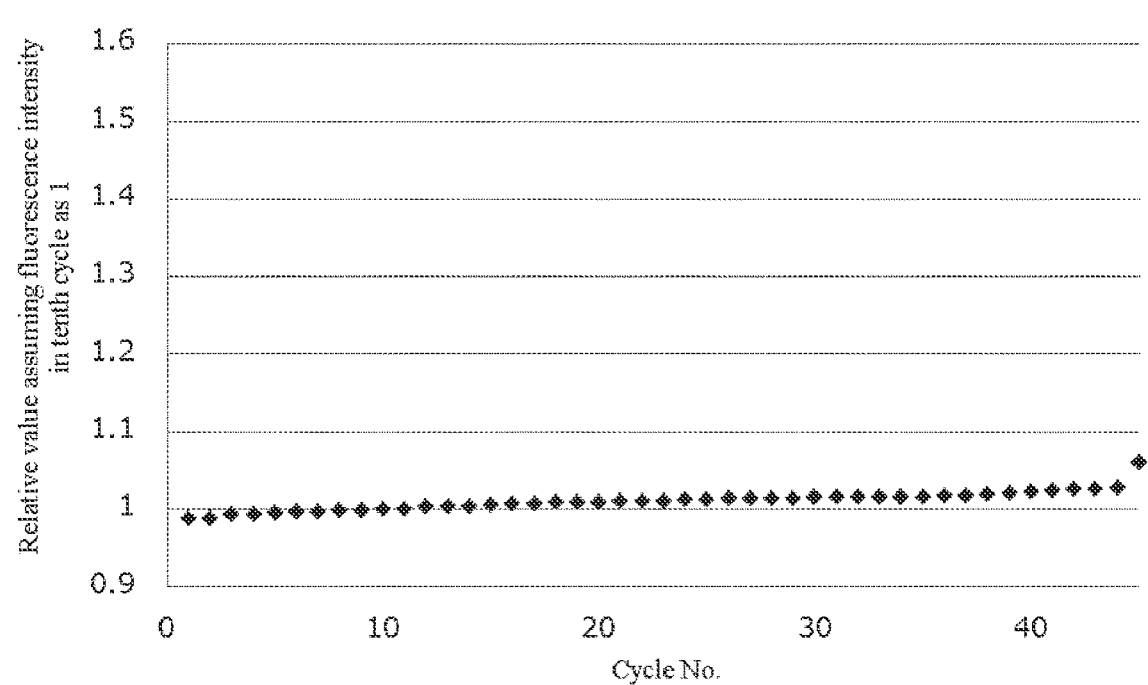
FIG. 18 is a graph showing changes of fluorescence intensity regarding a negative reference in Embodiment 4 according to the present invention.
Figure 19:
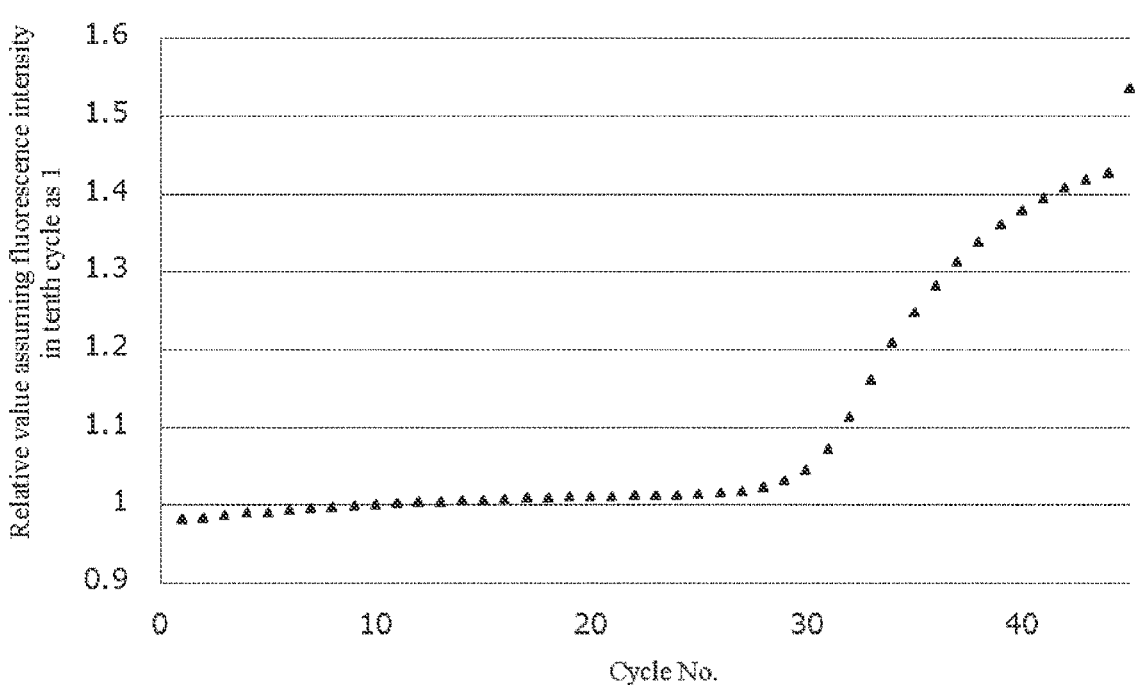
FIG. 19 is a graph showing changes of fluorescence intensity regarding a first target nucleic acid in Embodiment 4 according to the present invention.
Figure 20:
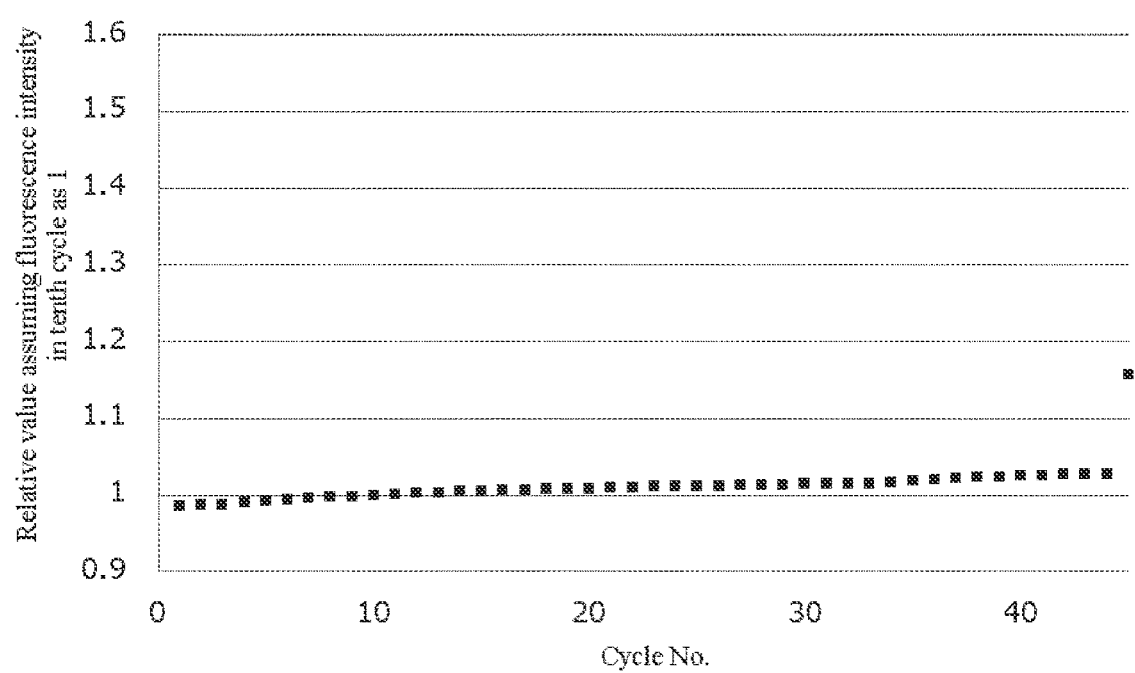
FIG. 20 is a graph showing changes of fluorescence intensity regarding a second target nucleic acid in Embodiment 4 according to the present invention.
Figure 21:
FIG. 21 is a graph showing changes of fluorescence intensity regarding the first target nucleic acid and the second target nucleic acid in Embodiment 4 according to the present invention.
Figure 21:
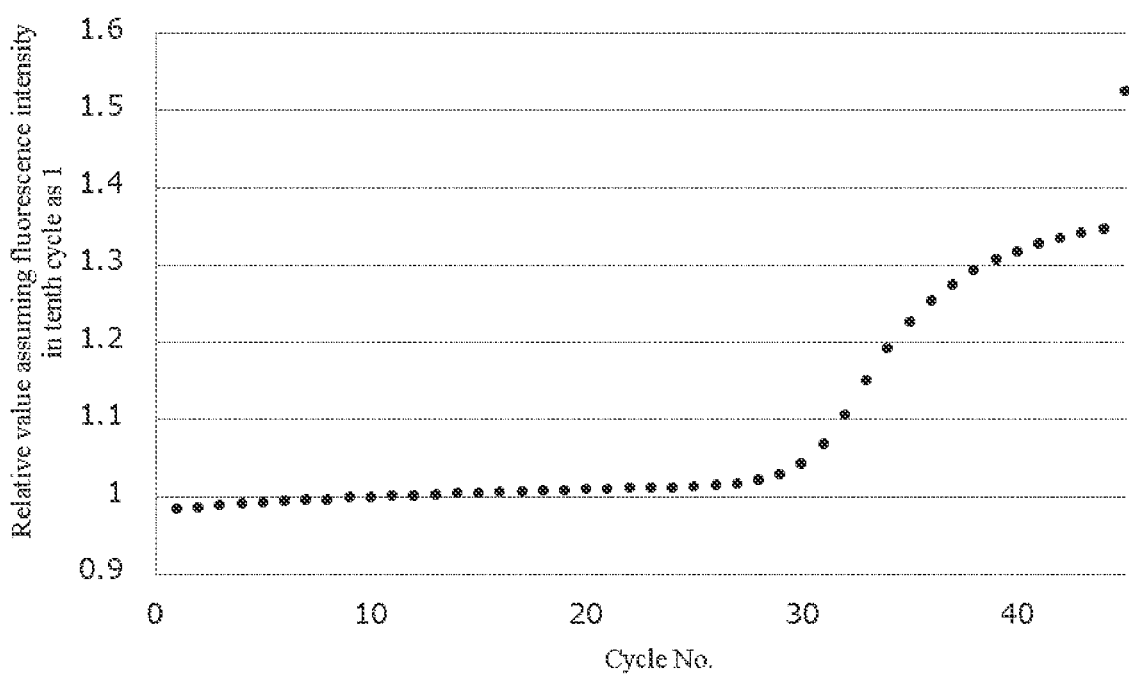
Figure 22:
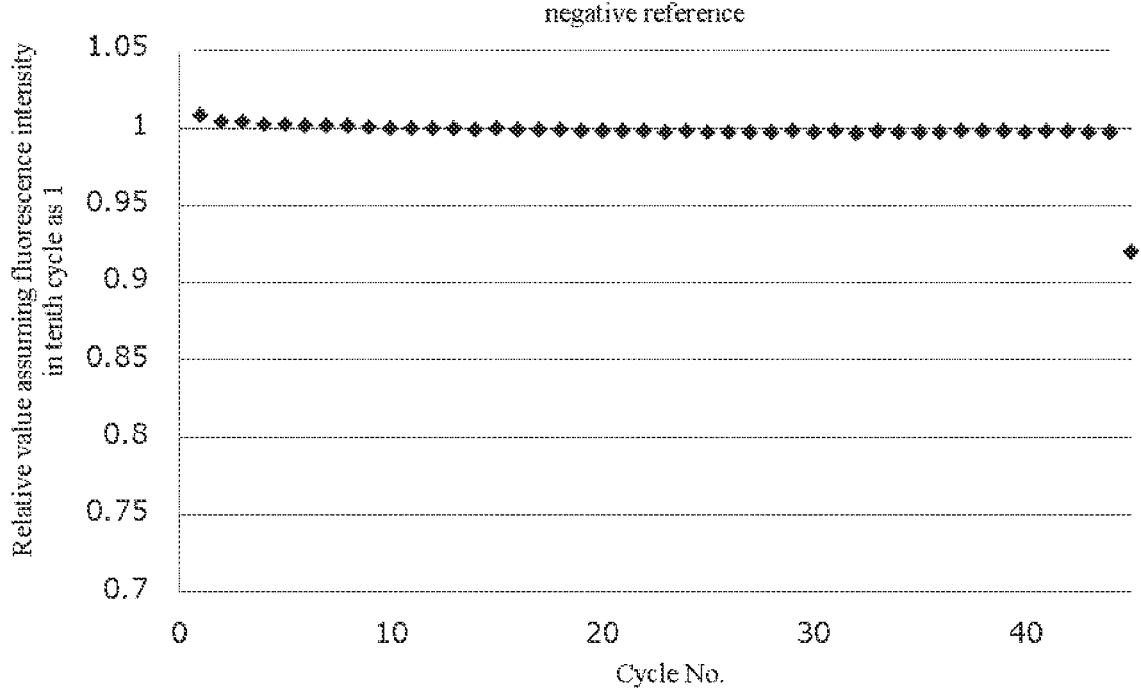
FIG. 22 is a graph showing changes of fluorescence intensity regarding a negative reference in Embodiment 5 according to the present invention.
Figure 23:
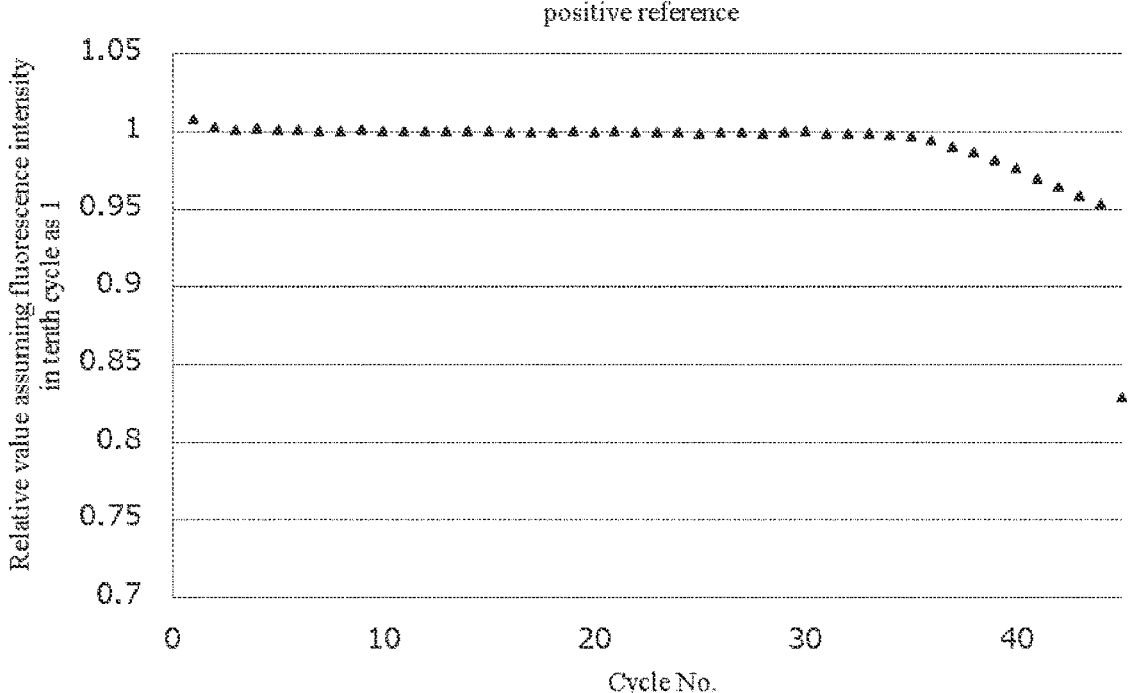
FIG. 23 is a graph showing changes of fluorescence intensity regarding a first target nucleic acid in Embodiment 5 according to the present invention.
Figure 24:
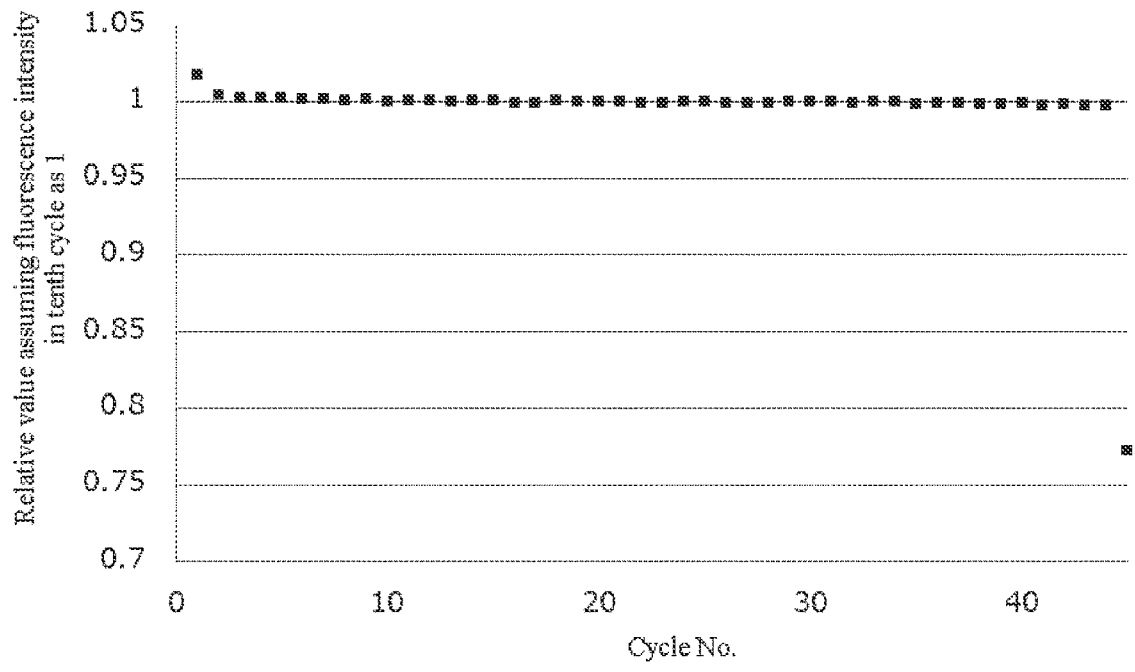
FIG. 24 is a graph showing changes of fluorescence intensity regarding a second target nucleic acid in Embodiment 5 according to the present invention.
Figure 25:
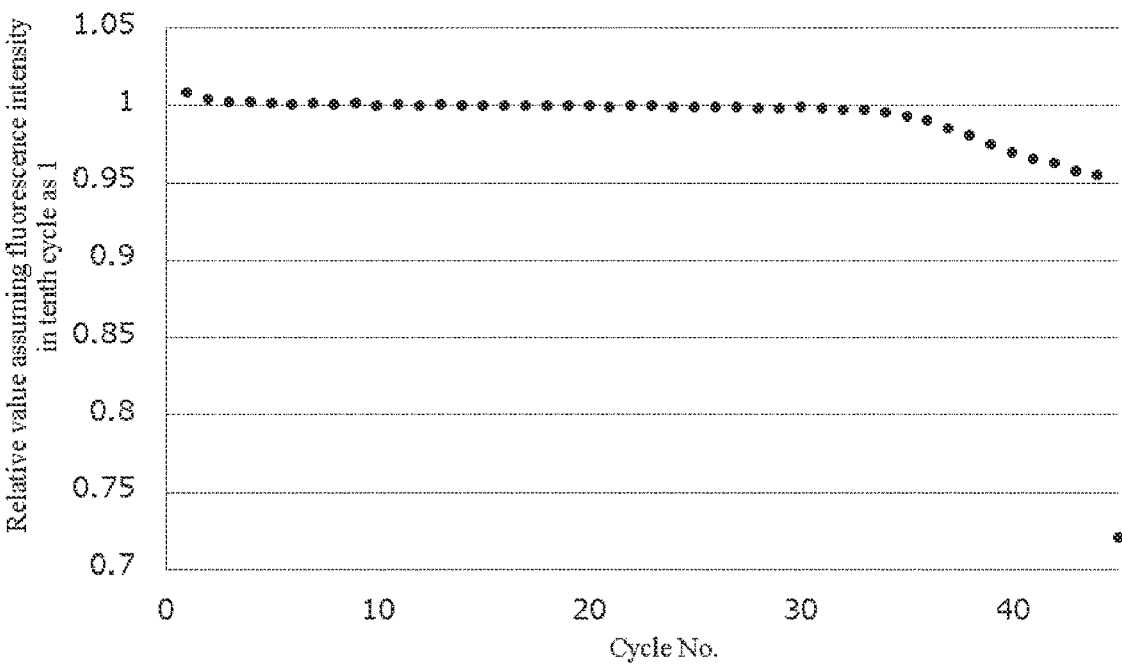
FIG. 25 is a graph showing changes of fluorescence intensity regarding the first target nucleic acid and the second target nucleic acid in Embodiment 5 according to the present invention.
Figure 26:
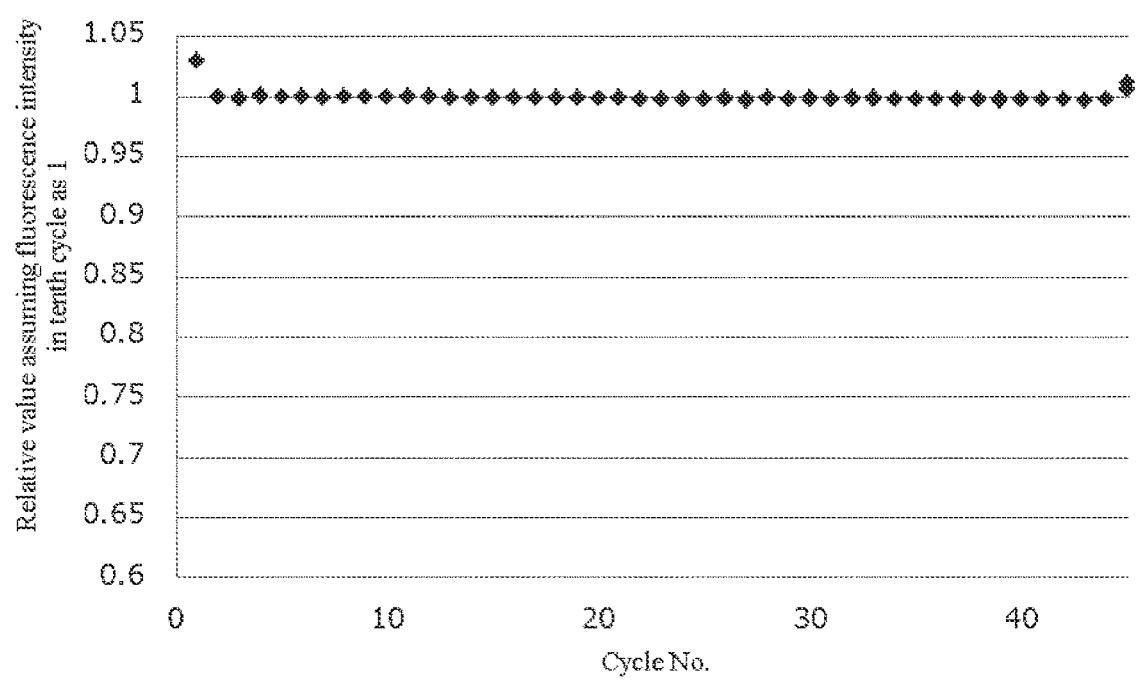
FIG. 26 is a graph showing changes of fluorescence intensity regarding a negative reference in Embodiment 6 according to the present invention.
Figure 27:
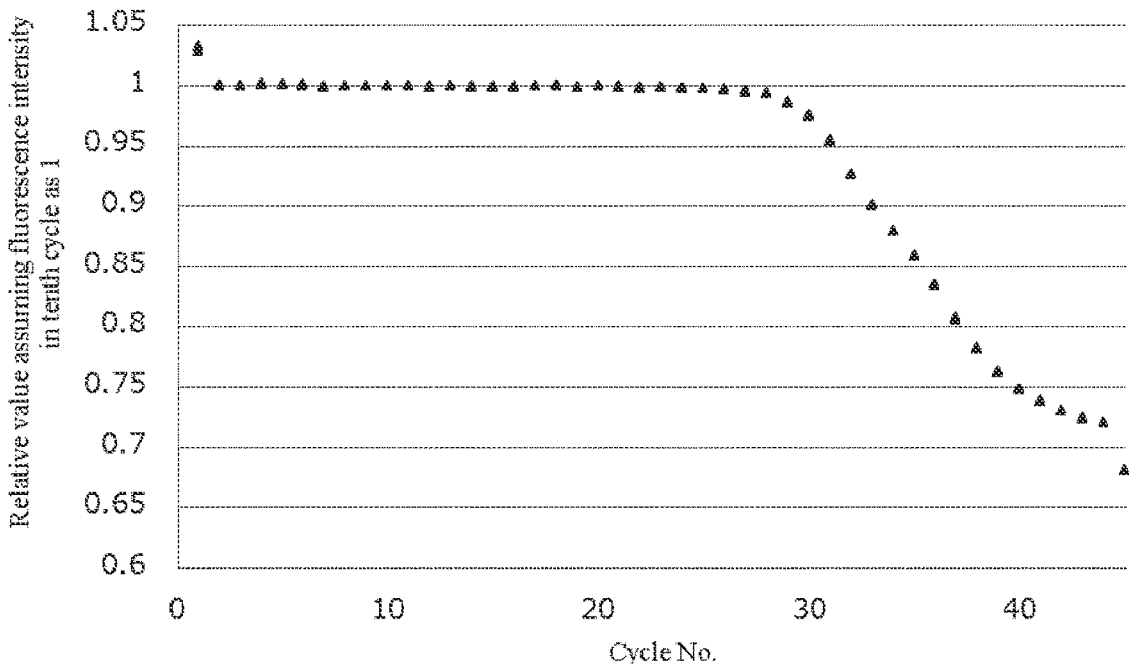
FIG. 27 is a graph showing changes of fluorescence intensity regarding a first target nucleic acid in Embodiment 6 according to the present invention.
Figure 28:
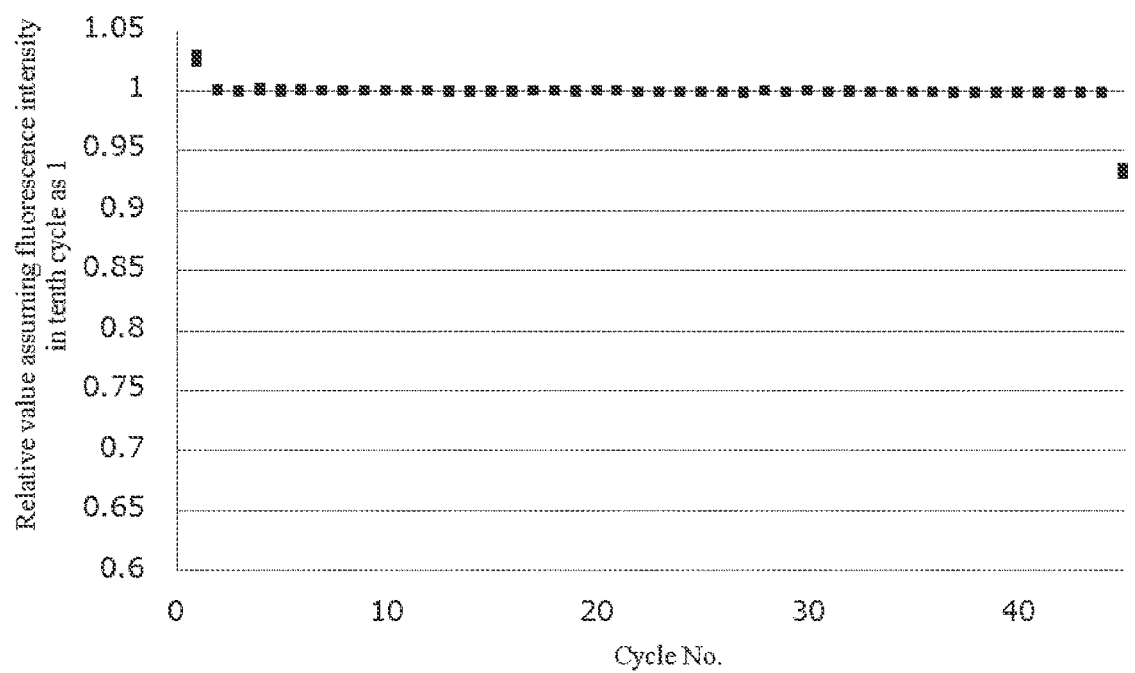
FIG. 28 is a graph showing changes of fluorescence intensity regarding a second target nucleic acid in Embodiment 6 according to the present invention.
Figure 29:
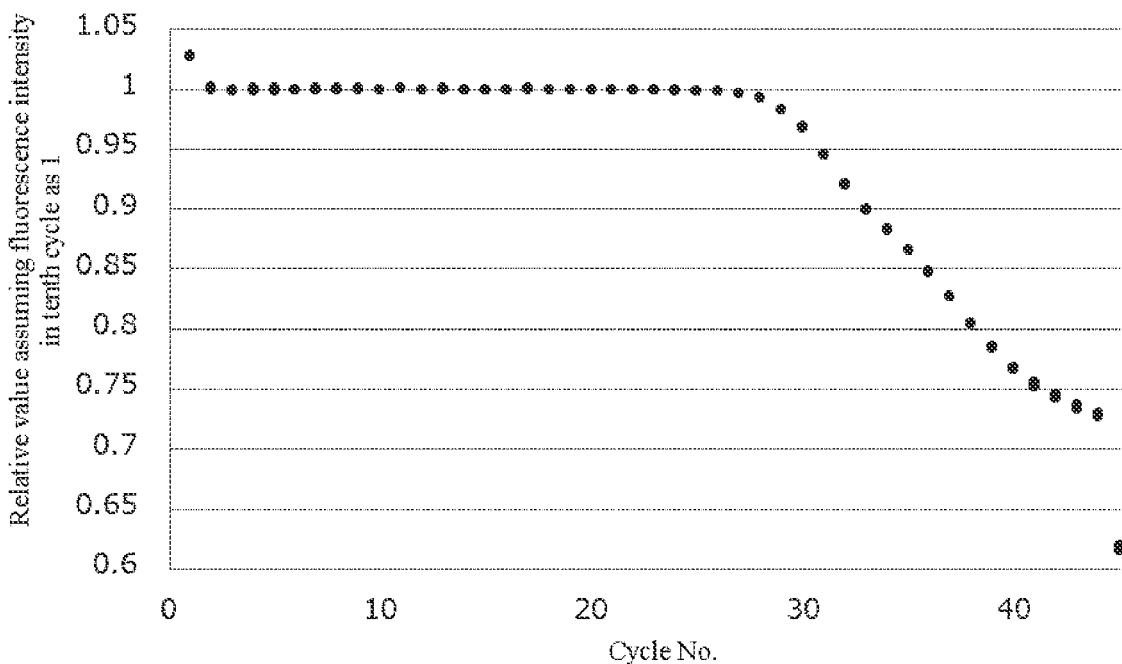
FIG. 29 is a graph showing changes of fluorescence intensity regarding the first target nucleic acid and the second target nucleic acid in Embodiment 6 according to the present invention.
Figure 30:
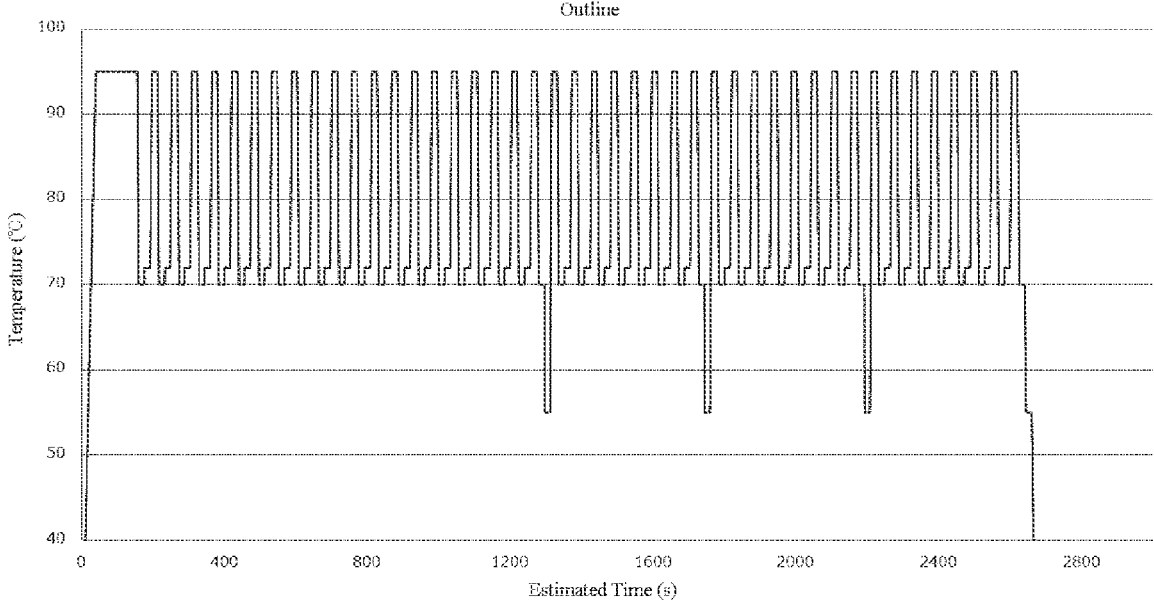
FIG. 30 is a graph showing changes of temperature within mixed-solution in Embodiment 7 according to the present invention.
Figure 31:
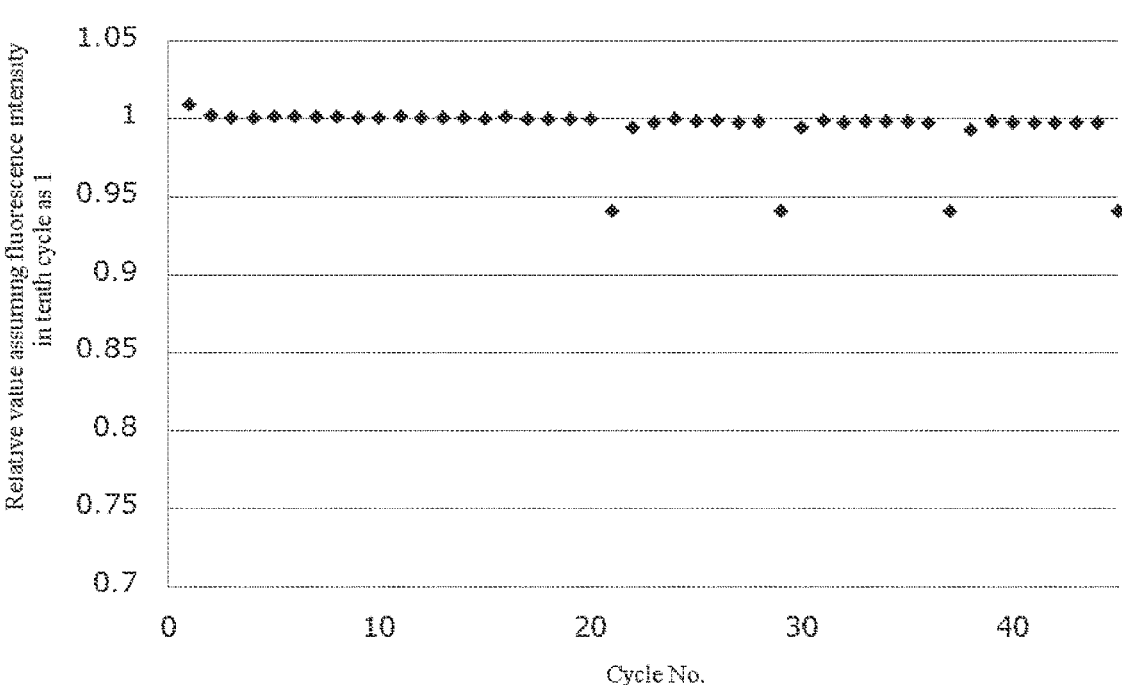
FIG. 31 is a graph showing changes of fluorescence intensity regarding a negative reference in Embodiment 7 according to the present invention.
Figure 32:
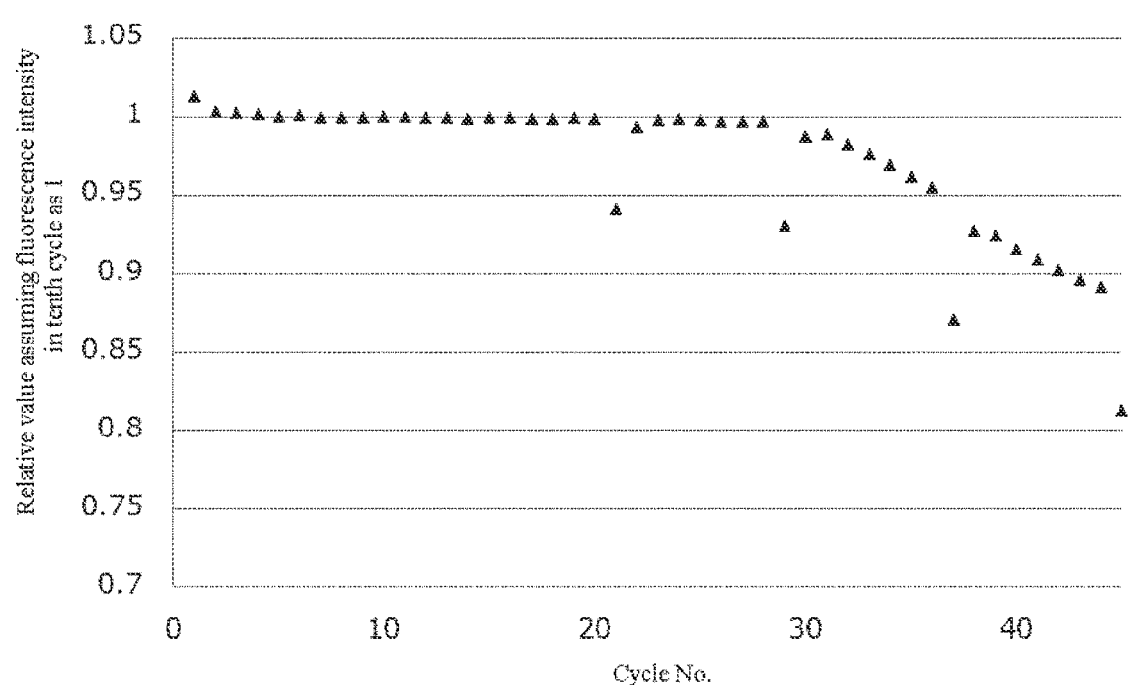
FIG. 32 is a graph showing changes of fluorescence intensity regarding a first target nucleic acid in Embodiment 7 according to the present invention.
Figure 33:
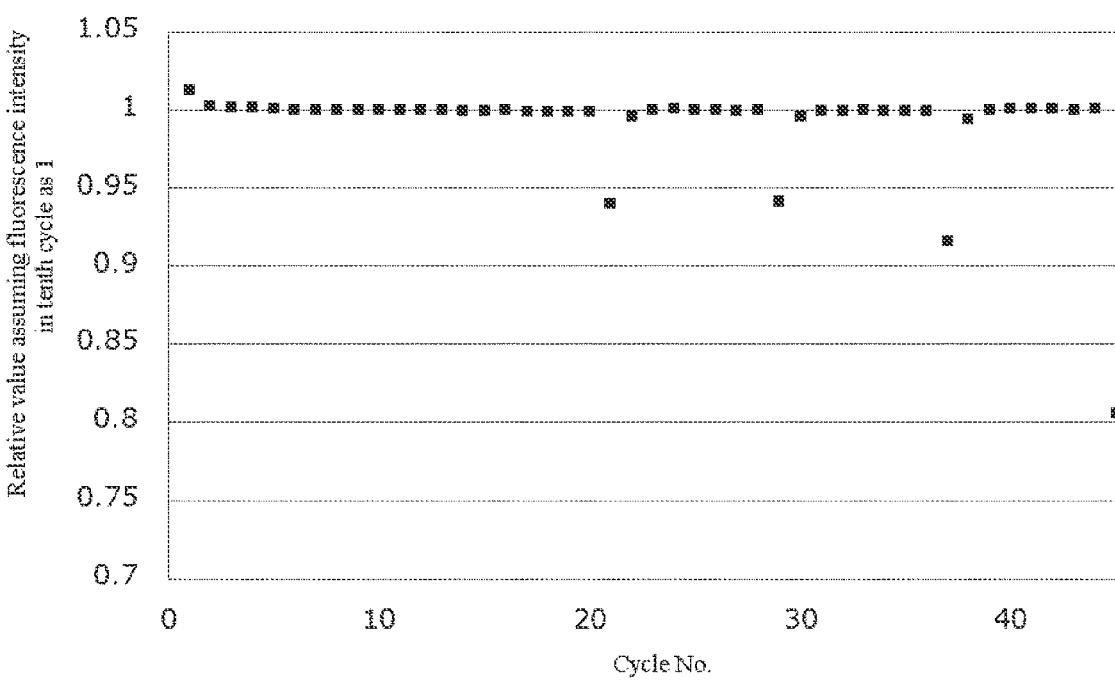
FIG. 33 is a graph showing changes of fluorescence intensity regarding a second target nucleic acid in Embodiment 7 according to the present invention.
Figure 34:
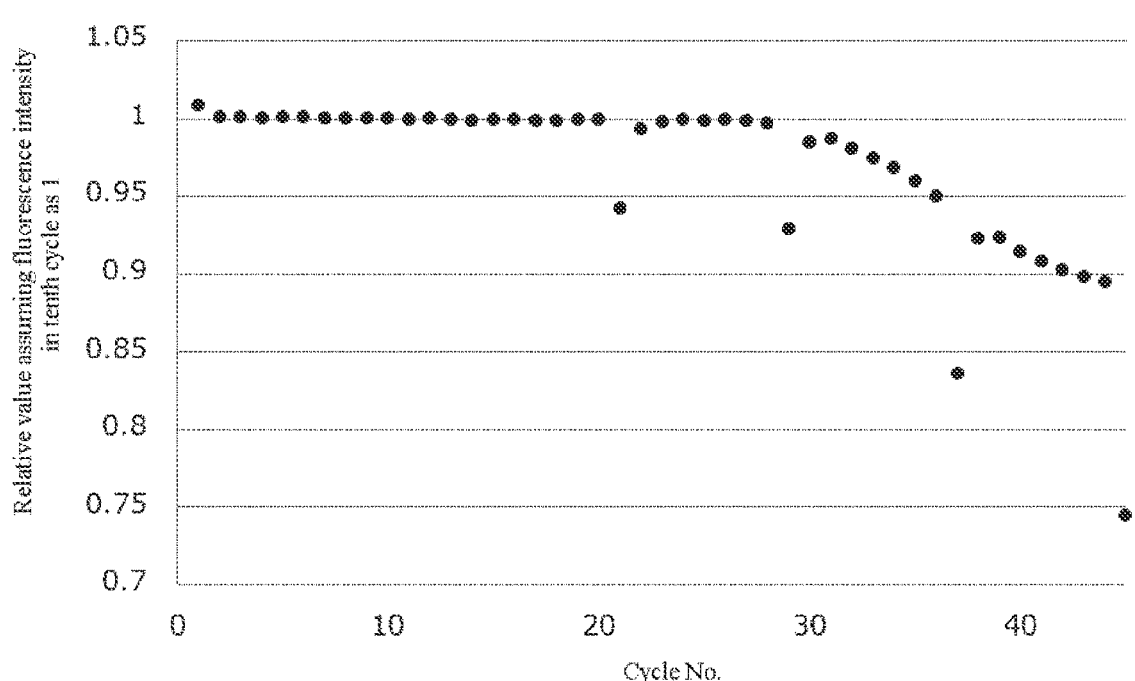
FIG. 34 is a graph showing changes of fluorescence intensity regarding the first target nucleic acid and the second target nucleic acid in Embodiment 7 according to the present invention.
Figure 35:
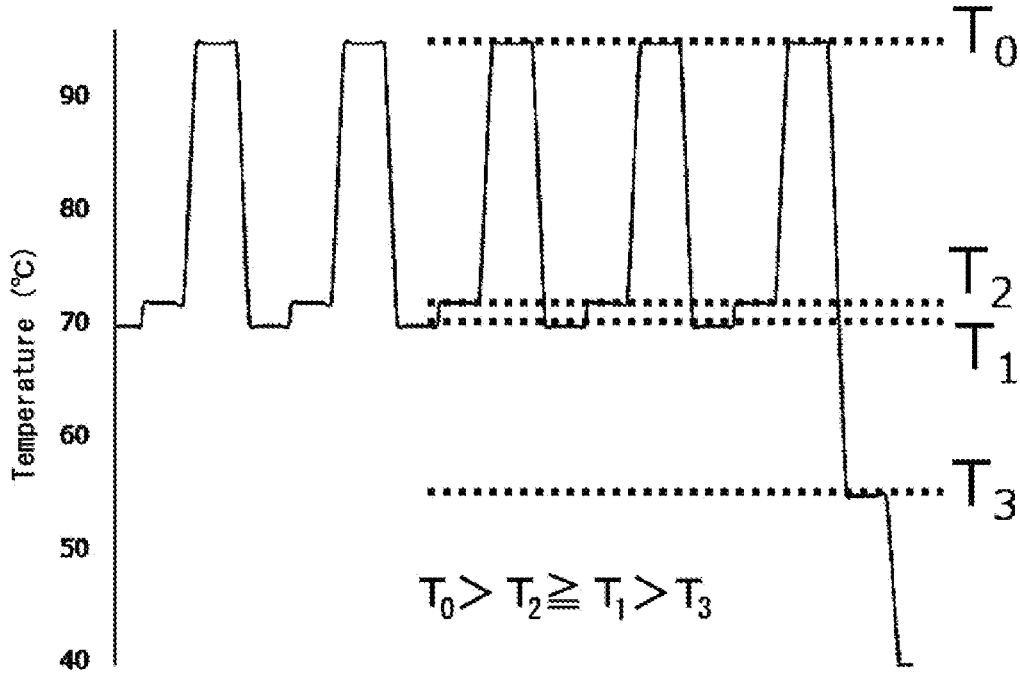
FIG. 35 is an enlarged view of changes of temperature in Embodiment 1 according to the present invention.
Figure 36:
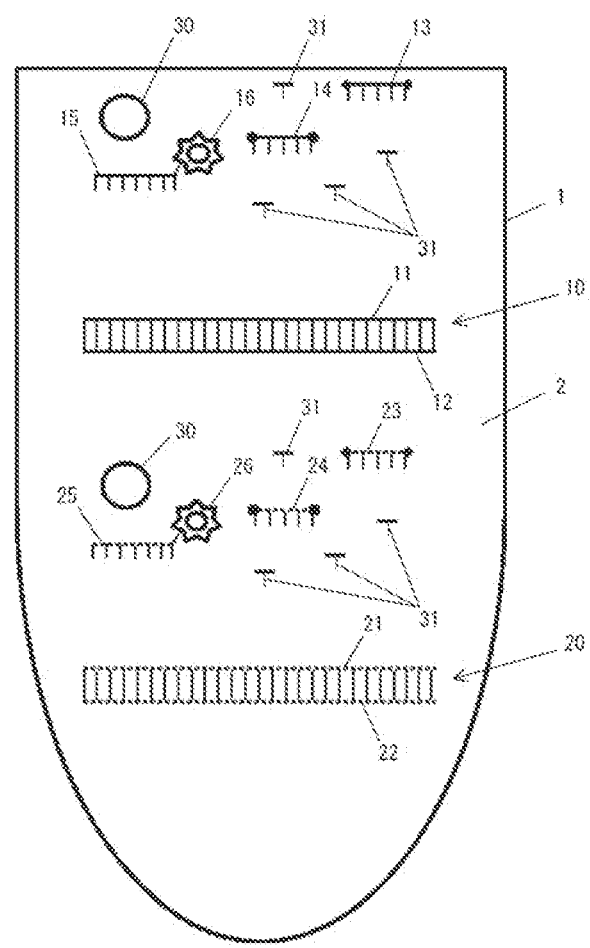
FIG. 36 is an explanatory diagram of mixed-solution composition in Embodiment 1 according to the present invention.
Figure 37A:
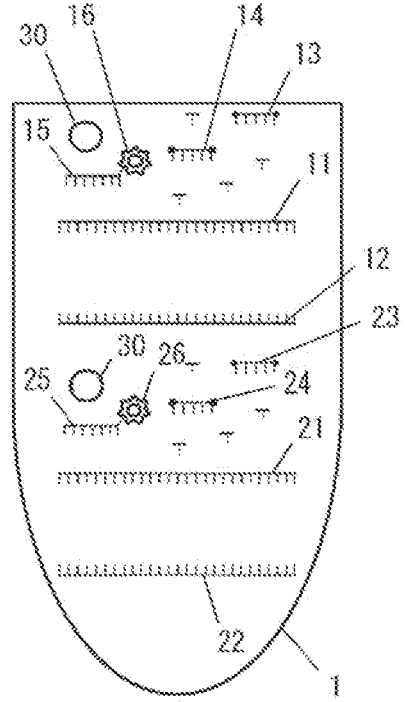
FIG. 37(*a*) is an explanatory diagram of a denaturation step in Embodiment 1 according to the present invention.
Figure 37B:
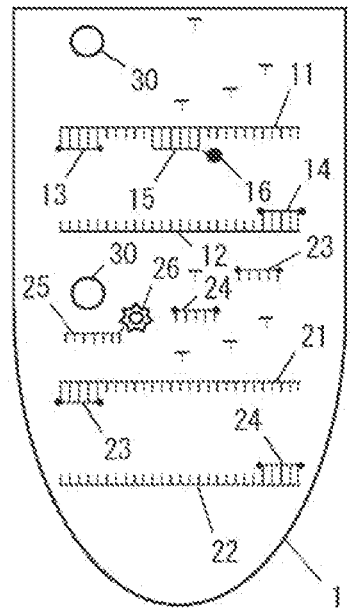
Figure 37C:
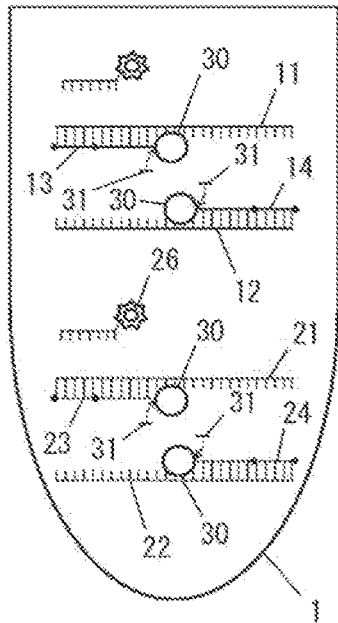
Figure 37D:
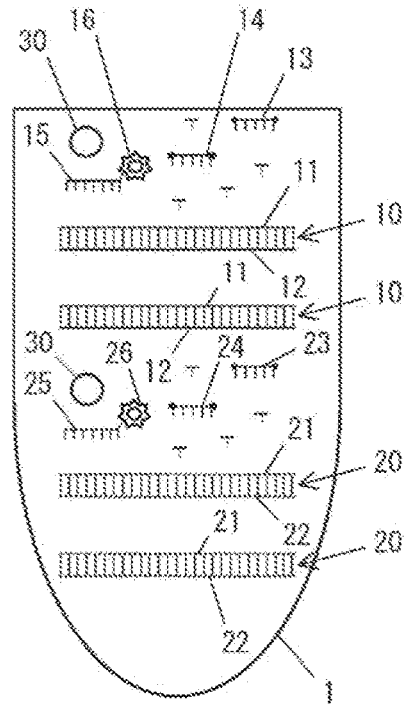
Figure 38A:
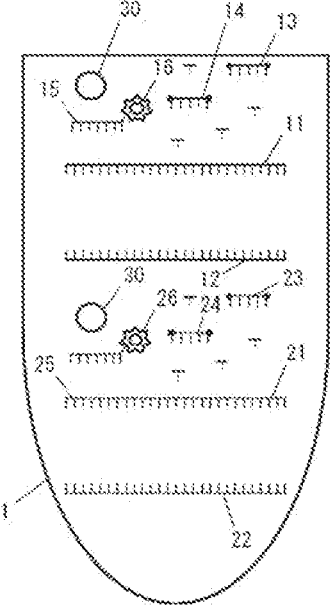
FIG. 38(*a*) is an explanatory diagram of the denaturation step in Embodiment 1 according to the present invention.
Figure 38B:
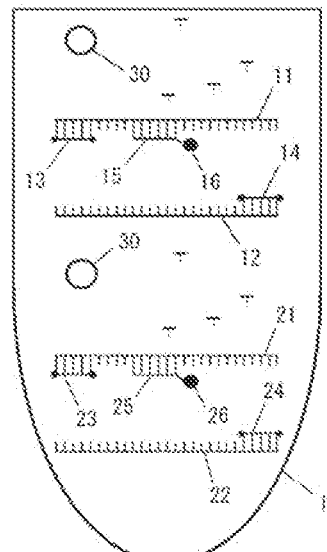

1: Vessel
2: Solution
10: First target nucleic acid
13: First target's F-primer
14: First target's R-primer
15: First target's probe
16: First labeling substance
20: Second target nucleic acid
23: Second target's F-primer
24: Second target's R-primer
25: Second target's probe
26: Second labeling substance
30: DNA polymerase
31: Deoxyribonucleoside triphoshate
T0: Denaturation temperature
T1: Annealing temperature
T2: Elongation temperature
T3: Second target detection temperature

The invention claimed is:

1. A detection method for detecting a first double stranded target nucleic acid and a second double stranded target nucleic acid differing from each other, comprising the steps of:

(a) subjecting a composition to an initial denaturation temperature, T0, wherein the composition comprises:

(i) a first target's primer for specifically hybridizing a first target nucleic acid and a second target's primer for specifically hybridizing a second target nucleic acid;

(ii) a first labeled probe for specifically detecting a first target nucleic acid and a second labeled probe for specifically detecting a second target nucleic acid, wherein the label of the first and second probe are identical; and (iii) double stranded first target nucleic acid and double stranded second nucleic acid and (iv) DNA polymerase and deoxyribonucleoside triphosphate;

(b) subjecting the composition to amplification of n cycles, wherein each cycle comprises the steps of:

(b1) dissociating the first double stranded target nucleic acid into single strands and denaturing the second double stranded target nucleic acid into single strands by subjecting the composition to the denaturation temperature, T0, and measuring the fluorescence signal from the first probe and second probe;

(b2) decreasing the temperature to an annealing temperature, T1, annealing the first target primer to each single strand of the first target nucleic acid and annealing the second target primer to each single strand of the second target nucleic acid and measuring the fluorescence signal of the first probe;

(b3) elongating the first target primer and the second target primer at an elongation temperature, T2, and measuring the fluorescence signal of the first probe;

(c) subjecting the composition to a step to detect the second target after the amplification cycles are complete, comprising the steps of:

(c1) increasing the temperature of the composition to denaturing temperature T0 and measuring the fluorescence intensity of the second probe; and (c2) decreasing the temperature of the composition and measuring the fluorescence signal from the second probe at a second target detection temperature, T3;

(d) comparing the fluorescence of the first probe to a first threshold value and the fluorescence of the second probe to a second threshold value comprising:

(d1) a first comparing step of comparing a first value of a measurement sample with a first threshold so as to judge that the first target nucleic acid is positive or negative, wherein said first threshold is a fluorescence intensity at the final amplification cycle for a negative reference sample;

(d2) a second comparing step of comparing a second value of the measurement sample with a second threshold so as to judge that the second target nucleic acid is positive or negative, wherein said second threshold is a fluorescence intensity for a reference sample negative for the second target nucleic acid;

and a step of capturing a difference caused by changes of the first and second fluorescent signals according to the second labeling substance so as to judge existence or non-existence of the second target nucleic acid;

wherein T0>T2≥T1>T3.

2. The detection method of claim 1, wherein for every cycle of amplification reaction and the second target detecting step, calculation is carried out according to formulae, including:

$$fn=fhyb.n/fden.n \qquad \text{(Formula 1); and}$$

$$fe=fhyb.e/fden.e \qquad \text{(Formula 1'),}$$

wherein:

fn: a fluorescence intensity value in an n-th cycle calculated according to Formula 1;

fhyb.n: a fluorescence intensity value at an elongation step in the n-th cycle;

fden.n: a fluorescence intensity value at a denaturation step in the n-th cycle;

fe: a fluorescence intensity value at the second target detecting step calculated according to Formula 1';

fhyb.e: a fluorescence intensity value (55 Centigrade) at the second target detecting step; and fden.e: a fluorescence intensity value (95 Centigrade) at the second target detecting step.

3. The detection method of claim 2, wherein the formulae further include:

$$Fn=fn/f10 \qquad \text{(Formula 2); and}$$

$$Fe=fe/f10 \qquad \text{(Formula 2'),}$$

wherein:

Fn: a relative value in the n-th cycle assuming that a fluorescence intensity value in a tenth cycle obtained according to Formula 1 is equal to a value of "1"; and Fe: a relative value at the second target detecting step assuming that the fluorescence intensity value in the tenth cycle obtained according to Formula 1' is equal to a value of "1".

4. The detection method of claim 1, wherein the fluorescent signals are shown by quenching light when the annealing occurs.

5. The detection method of claim 1, wherein the fluorescent signals are shown by emitting light when the annealing occurs.

6. The detection method of claim 1, wherein the first target nucleic acid is a *Mycoplasma pneumoniae* P1 genes and the second target nucleic acid is internal control composition.

7. The detection method of claim 1, wherein the first target nucleic acid is a *Chlamydia trachomatis* endogenous plasmid gene and the second target nucleic acid is a *Neisseria gonorrhoeae* CMT gene.

* * * * *